United States Patent [19]
Dominianni et al.

[11] Patent Number: 5,641,796
[45] Date of Patent: Jun. 24, 1997

[54] ORAL HYPOGLYCEMIC AGENTS

[75] Inventors: Samuel J. Dominianni; Lora L. Fitch; Klaus K. Schmiegel, all of Indianapolis, Ind.

[73] Assignee: Eli Lilly and Company, Indianapolis, Ind.

[21] Appl. No.: 332,667

[22] Filed: Nov. 1, 1994

[51] Int. Cl.$^6$ .................................................. C07D 413/10
[52] U.S. Cl. ........................ 514/374; 514/360; 514/364; 548/122; 548/129; 548/132; 548/143; 548/235
[58] Field of Search .......................... 514/374; 548/235, 548/263.2

[56] References Cited

U.S. PATENT DOCUMENTS

| | | | |
|---|---|---|---|
| 4,703,052 | 10/1987 | Eggler et al. | 514/337 |
| 4,753,956 | 6/1988 | Schnur | 514/365 |
| 4,791,125 | 12/1988 | Clark | 514/369 |
| 4,912,095 | 3/1990 | Kane et al. | 548/263.2 |
| 4,962,119 | 10/1990 | Boschelli et al. | 514/384 |
| 5,037,842 | 8/1991 | Goldstein | 514/375 |
| 5,066,662 | 11/1991 | Hobbs et al. | 514/364 |
| 5,130,379 | 7/1992 | Clark et al. | 514/333 |
| 5,155,122 | 10/1992 | Connor et al. | 514/363 |
| 5,183,825 | 2/1993 | Kees | 514/404 |
| 5,185,353 | 2/1993 | Turnbull et al. | 514/364 |
| 5,239,080 | 8/1993 | Sohda et al. | 548/236 |
| 5,254,576 | 10/1993 | Romine et al. | 514/365 |
| 5,334,604 | 8/1994 | Goldstein et al. | 514/364 |
| 5,376,670 | 12/1994 | Connor et al. | 514/383 |

FOREIGN PATENT DOCUMENTS

| | | |
|---|---|---|
| 177353 | 4/1986 | European Pat. Off. |
| 295828 | 12/1988 | European Pat. Off. |
| 306228 | 3/1989 | European Pat. Off. |
| 389699 | 10/1990 | European Pat. Off. |
| 415605 | 3/1991 | European Pat. Off. |
| 428312 | 5/1991 | European Pat. Off. |
| WO/92/03425 | 3/1992 | WIPO. |
| WO/93/00343 | 1/1993 | WIPO. |

OTHER PUBLICATIONS

Mullican et al., "Design of 5-(3,5-Di-tert-butyl-4-hydroxyphenyl)-1,3,4-thiadiazoles, -1,3,4-oxadiazoles, and -1,2,4-triazoles as Orally-Active, Nonulcerogenic Antiinflammatory Agents", *J. Med. Chem.*, 36, 1090–1099, (1993).
Momose et al., "Studies on Antidiabetic Agents. Synthesis and Biological Activities of Pioglitazone and Related Compounds", *Chem. Pharm. Bull.*, 39(6) 1440–1445, (1991).
Sohda et al., "Studies on Antibiabetic Agents. Synthesis of 5-[4-(1-Methylcyclohexylmethoxy)-benzyl]thiazolidine-2,4-dione (ADD-3878) and Its Derivatives", *Chem. Pharm. Bull.*, 30(10) 3580–3600, (1982).
Boschelli et al., "1,3,4-Oxadiazole, 1,3,4-Thiadiazole, and 1,2,4-Triazole Analogs of the Fenamates: In Vitro Inhibition of Cyclooxygenase and 5-Lipoxygenase Activities", *J. Med. Chem.*, 93, 1802–1810, (1993).
Ellingboe et al., "Antihyperglycemic Activity of Novel Substituted 3H-1,2,3,5-Oxathiadiazole 2-Oxides", *J. Med. Chem.*, 35, 1176–1183, (1992).
Ellingboe et al., "Antihyperglycemic Activity of Novel Naphthalenyl 3H-1,2,3,5-Oxathiadiazole 2-Oxides", *J. Med. Chem.*, 36, 2485–2493, (1993).
Unangst et al., "Novel 1,2,4-Oxadiazoles and 1,2,4-Thiadiazoles as Dual 5-Lipoxygenase and Cyclooxygenase Inhibitors", *J. Med. Chem.*, 35 3691–3698 (1992).
Gill et al., "Effects of Ciglitazone on Endogenous Plasma Islet Amyloid Polypeptide and Insulin Sensitivity in Obese-Diabetic Viable Yellow Mice", *Life Sciences*, vol. 48, No. 7, 703–710 (1991).
Girges et al., "Potentially Active Hypoglycemic Agents from $N^1$-Nicotinoyl-2-pyrazoline-5-one Derivatives and Their $N^1$-(Oxynictinoyl) Analogues", Stoffwechsel–Therapeutika Metabolism Therapeutics, Arzneim–Forsch Drug Res. 42 (II), Nr. 11, pp. 1350–1353 (1992).
Dow et al., "Benzyloxazolidine-2,4-diones as Potent Hypoglycemic Agents", *J. Med. Chem.*, 34(5), 1538–1544 (1991).
Hulin et al., "Novel Thiazolidine-2,4-diones as Potent Euglycemic Agents", *J. Med. Chem.*, 35, 1853–1864 (1992).
Zask et al., "Synthesis and Antihyperglycemic Activity of Novel 5-(Naphthalenylsulfonyl)-2,4-thiazolidinediones", *J. Med. Chem.*, 33(5), 1418–1423 (1990).
Sohda et al., "Studies on Antidiabetic Agents. Novel Thiazolidinedione Derivatives as Potent Hypoglycemic and Hypolipidemic Agents", *J. Med. Chem.*, 35(14) (1992).
Kees et al., "Perfluorocarbon–Based Antidiabetic Agents", *J. Med. Chem.*, 35(5) (1992).
Clark et al., "Substituted Dihydrobenzopyran and Dihydrobenzofuran Thiazolidine-2,4-diones as Hypoglycemic Agents", *J. Med. Chem.*, 34(1) (1991).

*Primary Examiner*—Donald G. Daus
*Attorney, Agent, or Firm*—Ronald S. Maciak; Roger S. Benjamin; David E. Boone

[57] ABSTRACT

Antihyperglycemic compounds selected from the group consisting of C-substituted pentacycloazoles and N-alkyl-substituted pentacycloazoles.

15 Claims, No Drawings

ORAL HYPOGLYCEMIC AGENTS

BACKGROUND OF THE INVENTION

This invention relates to C-substituted pentacycloazoles containing heteroatoms in the 2, 3 and 5 positions of the pentacycloazole ring and N-substituted pentacycloazoles containing nitrogen atoms in either the 2 and 4 positions or in the 3 position of the pentacycloazole ring.

Ellingboe et al. state in the *J. Med. Chem.*, Vol. 36, pages 2485–2493 (1993), which is hereby incorporated by reference, that drugs currently available for the control of the hyperglycemia associated with type 2 (non-insulin dependent) diabetes mellitus possess significant liabilities or efficacy limitations and that considerable effort has been directed toward the development of novel, orally active antihyperglycemic drugs. They also state that many of these new compounds incorporate a relatively acidic heterocycle which serves as the pharmacophore responsible for antihyperglycemic activity, such as thiazolidine-2,4-dione, tetrazole and oxazolidine-2,4-dione rings. In an earlier paper, *J. Med. Chem.* Vol. 35, pages 1176–1183 (1992), which is hereby incorporated by reference, Ellingboe et al. described a number of antihyperglycemic agents, which contain an acidic 3H-1,2,3,5-oxathiadiazole 2-oxide ring, appended via a methylene bridge to numerous aromatic systems. Kangi et al. E.P. 177, 353, which is hereby incorporated by reference, disclose antihyperglycemic thiazolidine pharmacophore appended via a methylene bridge to suitable aromatic systems.

The general object of this invention is to provide new antihyperglycemic compounds based on new pharmacophores. Other objects appear hereinafter.

In one aspect, this invention is an antihyperglycemic compound selected from the group consisting C-substituted pentacycloazole pharmacophore containing heteroatoms in the 2, 3 and 5 position of the pentacycloazole ring and N-substituted pentacycloazole pharmacophore containing nitrogen atoms in a position selected from the group consisting of the 2 and 4 positions of the pentacycloazole ring and the 3 position of the pentacycloazole ring.

In a second aspect, this invention is an antihyperglycemic composition comprising a pharmaceutically acceptable carrier, diluent or excipient and an effective amount of an antihyperglycemic compound selected from the group consisting C-substituted pentacycloazole pharmacophore containing heteroatoms in the 2, 3 and 5 position of the pentacycloazole ring and N-alkyl substituted pentacycloazole pharmacophore containing nitrogen or other hereto atoms in a position selected from the group consisting of the 2 and 4 positions of the pentacycloazole ring and the 3 position of the pentacycloazole ring.

In a third aspect, this invention is a method of reducing the hyperglycemia associated with non-insulin dependent diabetes mellitus which method comprises orally administering to a mammal, such as a human, a therapeutic dose of an antihyperglycemic compound selected from the group consisting C-substituted pentacycloazole pharmacophore containing heteroatoms in the 2, 3 and 5 position of the pentacycloazole ring and N-substituted pentacycloazole pharmacophore containing nitrogen atoms in a position selected from the group consisting of the 2 and 4 positions of the pentacycloazole ring and the 3 position of the pentacycloazole ring.

We have now found that the objects of this invention can be attained with antihyperglycemic compounds having a C-substituted pentacycloazole pharmacophore containing heteroatoms in the 2, 3 and 5 position of the pentacycloazole ring or an N-alkyl-substituted pentacycloazole pharmacophore (where the alkyl group has 1 to 12 carbon atoms) containing nitrogen atoms in both the 2 and 4 positions or in the 3 position of the pentacycloazole ring wherein the pentacycloazole ring is linked to a suitable aromatic system utilized with pharmacophores responsible for antihyperglycemic activity by an aliphatic group of 1 to 2 carbon atoms and a carbon atom of said aliphatic group is bonded directly to the pentacycloazole ring. Our studies have shown that other things being equal, many other compounds containing different pentacycloazole moieties, lack the antihyperglycemic activity of the compounds of this invention. Further, it appears that if the pentacycloazole moiety is linked to the same aromatic system by an isomeric aliphatic group having no carbon atom bonded to the pentacycloazole ring, the compound lacks antihyperglycemic activity. For example, when a —CH$_2$—S— linker was employed, the compound was inactive when the "S—" part of the linker was bonded to a C-pentacycloazole moiety and active when the "CH$_2$—" part of the linker was bonded to a C-pentacycloazole moiety. Likewise, when the pharmacophore was bonded directly to the aromatic moiety without an aliphatic linking group, the compounds were inactive.

While Mullican et al. in the *J. Med. Chem.*, Vol. 36, pages 1090–1099 (1993) disclose a C-substituted-2,3,5-triazole linked through methylene to a 4-hydroxy-3,5-dibutylphenyl moiety at page 1091 and Boschelli et al. in *J. Med. Chem.*, Vol. 36, pages 1802 to 1810 (1993) disclose a C-substituted pentacycloazole containing heteroatoms in the 2, 3 and 5 position linked through methylene to a dichlorophenylaminophenyl group moiety at page 1804, neither article describes or suggests that the compounds have antihyperglycemic activity. Further, to the best of our knowledge neither the 4-hydroxy-3,5-dibutylphenyl moiety nor the dichlorophenylaminophenyl group have been used with pharmacophores responsible for antihyperglycemic activity.

The compounds of this invention can be represented by the structure

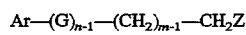

The bond of attachment to Z is assigned number 1 as described in the following schematic structure formula (I):

where each Q is independently C, N, O, or S as described in the following definition of Z.

Z is a C-substituted pentacycloazole containing heteroatoms in the 2, 3 and 5 positions of the pentacycloazole ring or an N-substituted (N at position 1) pentacycloazole containing N atoms in either the 2 and 4 positions or in the 3 position of the pentacycloazole ring; G is oxygen or sulfur; m and n are whole numbers ranging from 1 to 2; and Ar is a suitable aromatic system.

In somewhat greater detail, Z can have any of the structures inclusive of double bond tautomeric forms as follows:

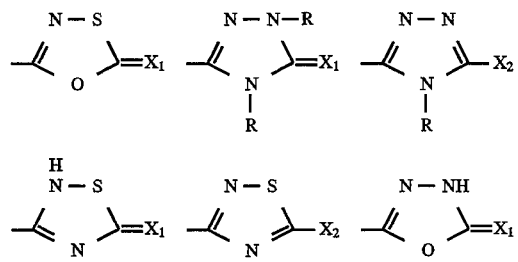

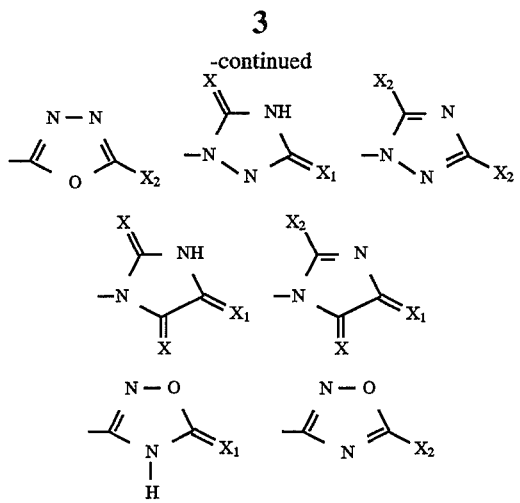

wherein $X_1$ is O or S; $X_2$ is —SR; and each R is independently selected from H, methyl, ethyl, propyl and butyl.

Ar can be any suitable aromatic system utilized with other pharmacophores responsible for antihyperglycemic activity such as those disclosed in the aforesaid Ellingboe et al. articles; the aforesaid Kangi et al. E.P. 177,353; Momose et. al. in *Chem. Pharm. Bull.*, Vol. 39, No. 6 at pages 1440 to 1445 (1991); Cantello et al. E.P. 415605; Clark et al. U.S. Pat. No. 4,791,125; Kees U.S. Pat. No. 5,183,825; Goldstein et al. WO 93/00343; Hindley E. P. 306,228 all of which are hereby incorporated by reference. Accordingly, the aromatic systems can range from simple dihydronaphthalene moieties in U.S. Pat. No. 5,183,825 to aromatic rings linked to heterocylic rings.

The preferred aromatic systems can be represented by the structure:

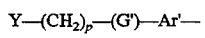

wherein Ar' is a divalent arylene moiety, such as phenylene, methyl substituted phenylene, chlorophenylene, etc.; G' is O or S; and Y is a cycloalkyl ring, such as methylcyclohexyl, a substituted or unsubstituted aryl group or a heterocyclic such as 2-phenyl-4-oxazolyl; p is a number from 1 to 6. An illustrative Y group is shown in formula (II):

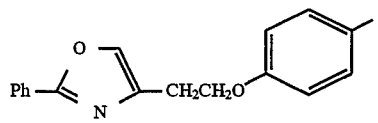

(II)

As is demonstrated in the Examples, the various C-substituted pentacycloazole compounds of this invention can be prepared by routine techniques. For example, C-substituted 2,3,5-triazoles can be prepared by reacting

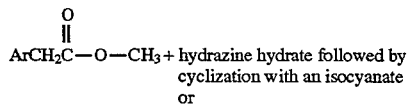

(1)

$ArCH_2C-O-CH_3$ + hydrazine hydrate followed by cyclization with an isocyanate or

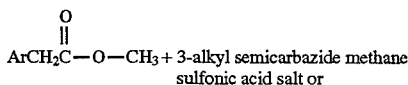

(2)

$ArCH_2C-O-CH_3$ + 3-alkyl semicarbazide methane sulfonic acid salt or

-continued $ArOH + BrCH_2COCH_3$ followed by hydrazine hydrate and then cyclized with an isocyanate or (3)

$ArOH + N,N$-dimethyl thiocarbamyl chloride (4)

thermally rearranged, hydrolyzed, followed by $BrCH_2COCH_3$ and then cyclization with an isocyanate, or $ArCH_2CH_2COCH_3$ + hydrazine hydrate followed by cyclization with an isocyanate, etc. (5)

A C-substituted 2,3-diazole can be prepared by reacting $ArCH_2CO_2R$+Hydrazine hydrate followed by cyclization with $CS_2$.

A C-substituted 2,5-diazole can be prepared by reacting $ArCH_2CN+CH_3OH+HCl$ to form $ArC(=NH_2)OCH_3^+Cl^-$ followed by Na in $CH_3OH$ to form an amidoxime and then treating with carbonyldiimidazole.

A C-substinuted-1,3,4-oxathiazolin-5-one can be prepared by converting

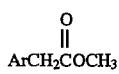

to the amide followed by cyclization with chlorocarbonyl-sulfenyl chloride.

A C-substituted 1,2,4-thiadiazolin-5-one can be prepared by reacting $ArC(=NH_2)OCH_3^+Cl^-$ described above with sodium hydride and cyclizing with chlorocarbonylsulfenyl chloride.

A N-substituted azole can be prepared either by reaction route (1) or (2) below:

(1) Reacting ArCHO with semicarbazide hydrochloride followed by reduction with boron hydride and cyclizing with carbonyldiimidazole or;

(2) Reacting $ArCH_2NH_2$ with sodium cyanate and cyclizing with diethyl oxylate.

The compounds of this invention and salts thereof exhibit excellent blood-glucose and blood-lipid lowering actions in mammals (e.g., mouse, rat, dog, cat, monkey, horse, and human beings), and show a low degree of toxicity in terms of both acute and subacute toxicities. Therefore, the compounds and salts thereof are of value to human beings for the treatment of hyperlipemia, diabetes and their complications.

The compounds of this invention are generally compounded with "pharmaceutically acceptable" carriers, diluents or excipients, which are compatible with the other ingredients of the formulation and not deleterious to the recipient thereof. The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg no about 50 mg/kg of body weight of an active compound of this invention. Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration. The compound can be administered by a variety of routes although oral is greatly preferred.

Pharmaceutical formulations of the invention are prepared by combining (e.g., mixing) a therapeutically effective amount of the compounds of the invention together with a pharmaceutically acceptable carrier or diluent therefor. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration. For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter. Sterile liquid form formulations include suspensions, emulsions, syrups and elixirs. The active ingredient can be dissolved or suspended in a pharmaceutically acceptable carrier, such as sterile water, sterile organic solvent or a mixture of both.

The active ingredient can also be dissolved in a suitable organic solvent, for instance aqueous propylene glycol. Other compositions can be made by dispersing the finely divided active ingredient in aqueous starch or sodium carboxymethyl cellulose solution or in a suitable oil.

The following Examples illustrate the preparation of compounds of the invention (unless otherwise indicated).

EXAMPLES

General Experimental Method:

Melting points are uncorrected. Thin Layer Chromatography was performed on silica plates. Reactions were conducted under an atmosphere of nitrogen. NMR spectra were obtained in $CDCl_3$ unless noted otherwise. Flash column chromatographies were performed over $SiO_2$.

2-(2-Phenyl-4-oxazolyl)ethanol was prepared as described in Example 12 Part A.

Example 1

Preparation of: 4-Methyl-5-[4-((2-(2-phenyl-4-oxazolyl) ethoxy)phenyl)methyl]1,2,4-triazolin-3-one.

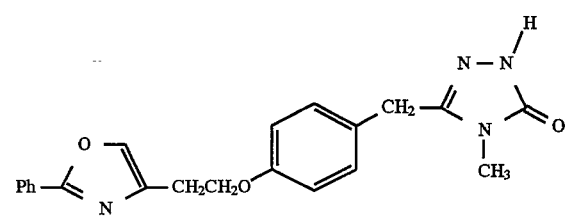

Part A

Preparation of: Methyl 4-[2-(2-phenyl-4-oxazolyl)ethoxyl] phenyl acetate.

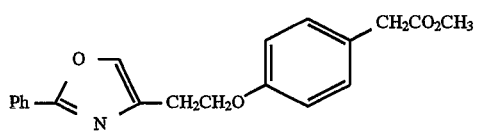

A stirred solution of 9.46 g 2-(2-phenyl-4-oxazolyl) ethanol, 8.34 g methyl(4-hydroxyphenyl)acetate, 13.10 g. triphenyl phosphine and 75 mL anhydrous THF (tetrahydrofuran) was treated dropwise with 7.9 mL diethyl azodicarboxylate over 15 minutes, allowing the temperature to rise spontaneously to 40°–50° C. The reaction was stirred at ambient temperature for 48 hours, treated with 2 mL of 30% $H_2O_2$, and evaporated in vacuo. The residue was extracted with boiling $Et_2O$ (ethyl ether), contacted with 75 mL of brine and dried over $MgSO_4$. After removal of the drying agent, the solvent was evaporated, the residue chromatographed, eluting with ethyl acetate-hexane. The product crystallized from ethylacetate-hexane to provide 14.8 g (88%), of a white solid mp 47°–48° C.

Anal. Cal. for $C_{20}H_{19}NO_4$: C, 71.20; H, 5.68; N, 4.15; Found: C, 71.43; H, 5.66; N, 4.07. IR 1734 $cm^{-1}$; NMR δ3.15 (t, 2H), 3.6 (s, 3H), 3.7 (s, 2H), 4.3 (t, 2H), 6.9 (d, 2H, (7.2 (d, 2H), 7.5 (m, 4H), 7.8 (s, 1H); MS:m/e 337.

Part B

Preparation of: 4-[2-2(2-phenyl-4-oxazolyl)-ethoxy]phenyl acetyl hydrazine.

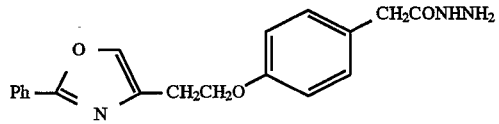

A stirred solution of 3.3 gm of methyl 4-[2-(2-phenyl-4-oxazolyl)ethoxy]phenyl acetate and 30 mL of MeOH was treated with 2.4 mL of 80% hydrazine hydrate, 0.5 gm of NaOMe and heated to reflux for 0.5 hour, during which time a copious precipitate formed. The cooled mixture was filtered and the white solid washed with MeOH and dried to provide 2.86 gm (86%) of product mp 163°–165° C.

Anal. Cal. for $C_{19}H_{19}N_3O_3$: C, 67.64; H, 5.68; N, 12.46. Found: IR 1648 $cm^{-1}$. MS/m/e 338. NMR 1.6 delta (broad m, 2H), 3.1 (t, 2H), 3.5 (s, 2H), 4.3 (t, 2H), 6.9 (d, 2H), 7.2 (d, 2H), 7.5 (m, 4H), 7.8 (s, 1H).

Part C

Preparation of: 4-Methyl-5-[4-((2-(2-phenyl-4-oxazolyl) ethoxy)phenyl)methyl]-1,2,4-triazolin-3-one.

The intermediate prepared in Example 1 Part B was suspended in 30 mL of THF (tetrahydrofuran), treated with 0.4 mL of methyl isocyanate and the stirred mixture heated to reflux for 2 hours. The mixture was cooled, diluted with Et₂O and filtered. The resulting white powder (0.97 gm, mp 191°–194° C.) was added to a solution prepared from 0.5 gm of Na metal and 25 mL of MeOH. The resulting solution was heated to reflux under an atmosphere of nitrogen for 5 hours, cooled and acidified with 1N HCl. The resulting precipitate was collected by filtration, washed with H₂O and dried. Recrystallization from THF-iPrOH provided 0.82 gm (86%) of product, mp 164°–167° C.

Anal. Cal. for $C_{21}H_{20}N_4O_3$: C, 67.01; H, 5.36; N, 14.88. Found: C, 66.75; H, 5.19; N, 14.63. Ir: 3302, 3072, 2933, 2854, 1691 cm⁻¹. Ms: m/e 376. NMR 1.7 (broad s, 1H, exchanges with D2O), 3.1 (s, 3H), 3.15 (t,2H), 3.85 (s,2H), 4.3 (t, 2H), 6.9 (d,2H), 7.2 (d,2H), 7.5 (m,4H), 7.8 (s,1H).

Example 2

Preparation of: 4-Ethyl-5-[4-((2-(2-phenyl-4-oxazolyl)ethoxy)phenyl)methyl]1,2,4-triazolin-3-one.

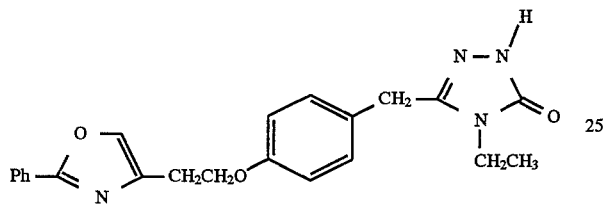

Method 1

A suspension of 1.5 gm of the intermediate prepared as in Example 1 Part B was suspended in 30 mL of THF, treated with 0.4 mL of ethyl isocyanate and refluxed for 2 hours. The mixture was cooled, diluted with Et₂O and filtered. The white solid was collected, washed with Et₂O and added to a solution prepared from 1.4 gm of 85% KOH and 100 mL of MeOH. The resulting solution was heated to reflux for 24 hours, at which time TLC (thin layer chromatography) showed complete consumption of starting material. The cooled solution was acidified with 1N HCl and the resulting precipitate collected by filtration. Recrystallization from ETOAc (ethyl acetate) provided 0.89 gm (51%) of product as white needles mp 139°–140° C.

Anal. Cal. for $C_{22}H_{22}N_4O_3$: C, 67.68; H, 5.68; N, 12.29. Found: C, 67.40; H, 5.78; N, 14.46. Ir: 1690 cm⁻¹. MS: m/e 390. NMR: delta 1.05 (t, 3H), 3.1 (t, 2H), 3.5 (1, 2H), 3.85 (s, 2H), 4.3 (t, 2H), 6.9 (d, 2H), 7.2 (d, 2H), 7.5 (m, 4H), 7.8 (s, 1H).

Method 2
Part A.

Preparation of: 3-Ethyl semicarbazide methanesulfonic acid salt.

A stirred solution of 25 gm tert-butyl carbazate in 200 mL CHCl₃ under nitrogen was treated dropwise over 0.5 hours with 16.5 mL ethyl isocyanate. The solution was stirred at room temperature 17 hours, treated with H₂O and the layers were separated. The aqueous layer was extracted with three 100 mL portions of CHCl₃ and the combined extracts were washed with brine, dried with Na₂SO₄, and filtered. Removal of the solvent in vacuo was followed by dissolution of the residue in 250 mL of dry THF. The resulting solution was treated dropwise with 22 mL of methane sulfonic acid over 0.5 hour. The resulting mixture was stirred at ambient temperature for 36 hours, during which time a precipitate formed. The solid was filtered and washed with THF and Et₂O to provide 24.2 gm (86%) of the salt mp 115°–118° C.

NMR: delta 1.04 (t, 3H), 2.37 (s, 3H), 3.10 (q, 2 h), 7.08 (t, 1H), 8.59 (s, 1H), 9.76 (broad s, 2H)>MS: m/e 103 (=M—$CH_3SO_3H$).

Part B

To a solution prepared from 6.82 gm of Na metal and 200 mL of MeOH were added 2.95 gm of the salt from Method 2 Example 2 Part A and 5 gm of the intermediate prepared as in Example 1, Part A. The resulting mixture was refluxed for 100 hr, cooled and evaporated in vacuo. The residue was treated with 200 mL 2N HCl and extracted with three 100 mL portions of ETOAc. The combined extracts were washed with H₂O, brine, dried with Na₂SO₄, filtered, and the solvent removed in vacuo. Chromatography of the residue over silica produced 1.5 gm (26%) of product identical to the material prepared in Method 1.

Example 3

Preparation of: 4-n-Butyl-5-[4-((2-(2-phenyl-4-oxazolyl)ethoxy)phenyl)methyl]1,2,4-triazolin-3-one.

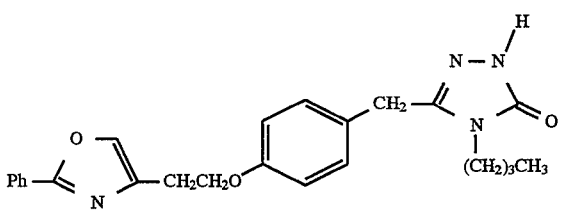

A suspension of 1.6 gm of the intermediate prepared as in Example 1 Part B in 40 mL of THF was treated with 0.8 mL of n-butyl isocyanate and heated to reflux for 2 hours. The cooled mixture was diluted with Et₂O and filtered. The white powder (1.9 gm, mp 172°–175° C.) was added to a solution prepared from 3.8 gm 85% KOH and 30 mL of MeOH and the resulting solution refluxed for a total of 48 hours. The cooled solution was acidified with 1N HCl and the soft white powder collected by filtration, washed with H₂O and dried. Recrystallization from i-PrOH-Hexane provided 1.01 gm (51%) of product mp 120°–122° C.

Anal.: Cal. for $C_{24}H_{26}N_4O_3$. C, 68.88; H, 6.26; N, 13.39. Found: C, 68.63; H, 6.42; N, 12.82. MS: m/e 418. IR: 3401, 3063, 3063, 1702 cm⁻¹. NMR: 0.9 (t, 3H), 1.3 (m, m, 2H), 1.45 (m, 2H), 1.7 (broad s, 1H, exchanges with D₂O), 3.1 (t, 2H), 3.5 (t, 2H), 3.85 (s, 2H), 4.3 (t, 2H), 6.9 (d, 2H), 7.2 (d, 2H), 7.5 (m, 4H), 7.8 (s, 1H).

Example 4

Preparation of: 4-Methyl-5-[4-((2-(2-phenyl-4-oxazolyl)ethoxy)phenyl)methyl]1,2,4-triazolin-3-thione.

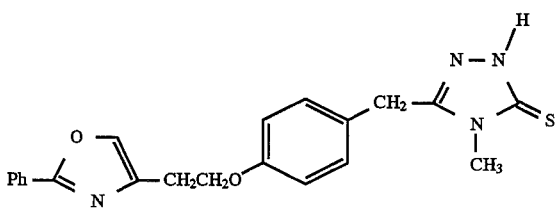

Method 1

The intermediate prepared as in Example 1 Part 1 (2.48 gm) and 0.80 gm of 4-methyl thiosemicarbazide were added to a solution prepared from 0.72 gm of Na metal and 20 mL of MeOH. The resulting yellow solution was refluxed for 2 hours, cooled and acidified with 1N HCl. The resulting white precipitate was collected, washed with H$_2$O and dried. Recrystallization from THF-H$_2$O and from EtOAc provided 0.82 gm (28%) of 4-methyl-5-[4-((2-phenyl-4-oxazolyl) ethoxy)phenyl)-methyl]-1,2,4-triazolin-3- thione. mp 189°–190° C.

Anal.: Cal. for C$_{21}$H$_{20}$N$_4$O$_2$S: C, 64.27; H, 5.14; N, 14.27. Found: C, 64.41; H, 5.22; N, 14.00. IR: 3099, 3042, 2939, 2878, 1574 cm$^{-1}$. MS: m/e 392. NMR: delta 3.1 (t, 2H), 3.35 (s, 3H), 4.0 (s, 2H), 4.3 (t, 2H), 6.9 (d, 2H), 7.2 (d, 2H), 7.5 (m, 4H), 7.8 (s, 1H).

Method 2

A stirred suspension of 1.35 gm of the intermediate prepared as in Example 1 Part B in 30 mL of THF was treated with 0.7 gm of methyl isothiocyanate and heated to reflux for 1 hour. The precipitate which formed on cooling was filtered and washed with ether. This solid (1.44 gm, mp 175°–177° C.) was added to a solution prepared from 0.8 gm of Na metal and 25 mL of MeOH and the resulting solution refluxed for 2 hours. The cooled solution was acidified with 1N HCl and the resulting precipitate collected. Recrystallization from ETOAc provided 1.2 gm (76%) of 4-methyl-5-[4-((2-(2-phenyl-4-oxazolyl)ethoxy)phenyl)methyl]-1,2,4-triazolin-3-thione. mp. 189°–190° C., identical to that prepared in Example 4 Method 1.

Example 5

Preparation of: 1(3)H-5-[4-((2-(2-phenyl-4-oxazolyl)ethoxy)phenyl)methyl]1,2,4-triazolin-3-thione

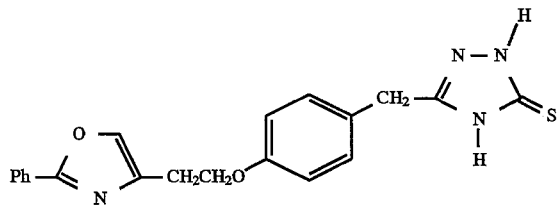

Thiosemicarbazide (1.90 gm) and 2.0 gm of the intermediate prepared as in Example 1 part A were added to a solution prepared from 0.6 gm of Na metal and 20 mL of 1-PrOH. The resulting mixture was heated to reflux for 3 hours and kept at room temperature overnight. The cooled mixture was acidified with 1N HCl and the solid filtered. Recrystallization from THF-MeOH provided 1.2 gm (53%) of product as a white solid mp 228°–230° C.

Anal.: Cal. for C$_{20}$H$_{18}$N$_4$O$_2$S: C, 63.47; H, 4.79; N, 14.80. Found: C, 63.73; H, 4.85; N, 14.78. IR: 3096, 3029, 2928, 2877, 1609 cm$^{-1}$. MS: m/e 378. NMR: delta 3.1 (t, 2H), 4.0 (broad s, 2H exchanges with D$_2$O), 4.3 (t, 2H), 6.9 (d, 2H), 7.2 (d, 2H), 7.5 (m, 4H), 7.8 s, 1H).

Example 6

Preparation of: 3-Methylthio-4-methyl-5-[4-((2-(2-phenyl-4-oxazolyl)ethoxy)phenyl)methyl]1,2,4-triazoline.

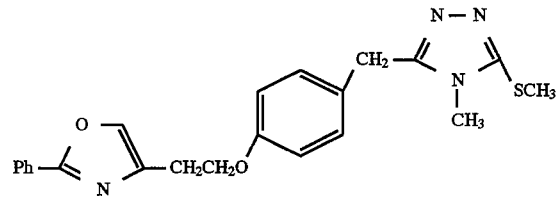

A stirred suspension of 2.42 gm of the intermediate prepared as in Example 1 Part B in 40 mL THF was treated with 2.1 gm of methyl isothiocyanate and refluxed for 3 hours. The reaction mixture was cooled and the solid filtered and washed with Et$_2$O. This solid was then added to a solution prepared from 1.5 gm of Na metal and 80 mL of MeOH and the resulting solution refluxed for 2 hours. The solution was allowed to cool with protection from atmospheric oxygen and treated with 5 mL of CH$_3$I. The resulting mixture was kept at room temperature overnight, treated with H$_2$O and extracted with three 125 mL portions of EtOAc. The combined extracts were washed with H$_2$O, brine, dried over MgSO$_4$ and evaporated to provide an oil which solidified on standing. Crystallization from EtOAc-hexane with the aid of decolorizing carbon provided 1.62 gm (56%) of the product as glittering flakes mp 110°–112° C.

Anal.: Cal. for C$_{22}$H$_{22}$N$_4$O$_2$S: C, 65.00 H, 5.45; N, 13.78. Found: C, 64.61; H, 5.44; N, 13.59. IR: 2914, 1550 cm$^{-1}$. MS: m/e 406. NMR: delta 2.7 (s, 3H), 3.1 (t, 2H), 3.3 (s, 3H), 4.15 (s, 2H), 4.3 (t, 2H), 6.9 (d, 2H), 7.2 (d, 2H), 7.5 (m, 4H, 7.8 (s, 1H).

Example 7

Preparation of: 4-Methyl-5-[4-((2-(2-phenyl-4-oxazolyl)ethoxy)phenyl)2-oxaethyl]1,2,4-triazolin-3-one.

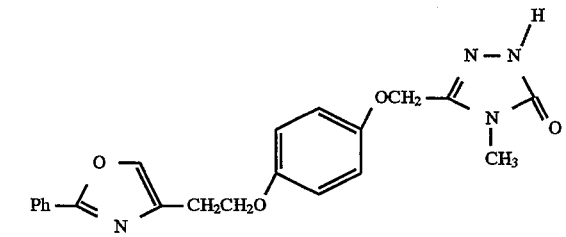

Part A.

Preparation of; 5-[(2-(2-Phenyl-4-oxazolyl)-ethoxyphenyl)] benzyl ether

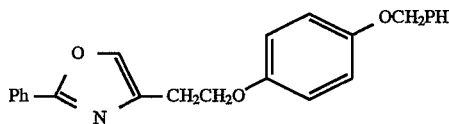

A stirred solution of 38.7 gm 4-benzyloxyphenol, 37.4 gm triphenyl phosphine, 27.4 gm 2-(2-phenyl-4-oxazolyl) ethanol and 200 mL THF was treated dropwise with 25 gm of diethyl azodicarboxylate over 0.25 hours, allowing the temperature to rise spontaneously to 50°–60° C. The solution was kept at room temperature for 72 hours, treated with 2 mL of 30% H$_2$O$_2$ and the solvent removed in vacuo. The solid residual mass was dissolved in 350 mL of boiling EtOH and allowed to cool slowly. The white crystals which precipitated were filtered and washed with small portions of EtOH to provide 39.1 gm (75%) of needles mp 108°–112° C.

Anal: Cal. for C$_{24}$H$_{21}$NO$_3$; C, 77.61; H, 5.70; N, 3.77. Found: C, 77.35; H, 5.75; N, 3.50.MS: m/e 371.

Part B.

Preparation of: 4-[2-(2-phenyl-4-oxazolyl)ethox]phenol.

A solution of the intermediate prepared in Example 7 Part A in 240 mL ETOH/280 mL THF was hydrogenated with 4 gm of 5% Pd/C at room temperature overnight with an initial hydrogen pressure of 60 psi (413.7 KPa). After removal of the catalyst by filtration, the solvents were removed in vacuo and the residue crystallized from i-PrOH to provide 24.7 gm (83%) mp 171°–176° C.

Anal.: Cal. for $C_{17}H_{15}NO_3$: C, 72.58; H, 5.38; N, 4.98. Found: C, 72.31; H, 5.40; N, 5.01. MS: m/e 281.

Part C

Preparation of: Methyl O-4-[2-(2-phenyl-4-oxazolyl) ethoxy]phenylglycolic acid hydrazide.

A stirred solution of 5.40 gm of the intermediate from Example 7 Part B in 75 mL of methyl ethyl ketone was treated with 4 mL of methyl bromoacetate, 1.2 gm powdered KI, 11.1 gm powdered $K_2CO_3$ and heated to reflux for 4 hours. The cooled mixture was diluted with $H_2O$, brine, dried over $MgSO_4$, filtered, and evaporated to provide an oil which solidified on trituration with hexane, mp 62°–66° C. A solution of 2.36 gm of this solid in 25 mL MeOH was treated with 2 mL of 85% hydrazine hydrate, 0.2 gm of NaOMe and refluxed 1 hour; during which time a thick precipitate formed. The cooled mixture was filtered and the solid washed with MeOH and $Et_2O$ to provide 2.20 gm (93%) of white powder mp 151°–154°.

Anal.: Cal. for $C_{19}H_{19}N_3O_4$: C, 64.58; H, 5.42; N, 11.89. Found: C, 64.71; H, 5.64; N, 11.70. MS: m/e 353.

Part D

A stirred suspension of 1.46 gm of the intermediate from Example 7 Part C in 20 mL THF was treated with 1 mL methyl isocyanate and refluxed for 1 hour. The cooled mixture was diluted with $Et_2O$ and filtered. The fine white powder was washed with $Et_2O$; mp 180°–182° C. This solid was added to a solution prepared from 3.9 gm of 85% KOH/30 mL MeOH and the resulting solution refluxed 4 hours. An additional 1.8 gm of 85% KOH was added and the mixture refluxed an additional 3 hours, kept at room temperature overnight and acidified with 2N HCl. The solid obtained by filtration was washed with $H_2O$ and dried to provide 0.94 gm (58%) of 4-methyl-5-[4-((2-(2-phenyl-4-oxazolyl)ethoxy)phenyl)2-oxaethyl]1,2,4-triazolin-3-one mp 137°–140° C.

Anal.: Cal. for $C_{21}H_{20}N_4O_4$: C, 64.28; H, 5.14; N, 14.27. Found: C, 64.48; H, 5.27; N, 14.04. MS: m/e 392. IR:1712, 1685 cm$^{-1}$. NMR: delta 3.1 (t, 2H), 3.35 (s, 3H), 4.3 (t, 2H), 4.9 (s, 2H), 6.9 (d, 2H), 7.2 (d, 2H), 7.5 (m, 4H), 7.8 (s, 1H), 9.5 (broad s, 1H, exchanges with D2O).

Example 8

Preparation of: 4-Methyl-5-[4-((2-(2-phenyl-4-oxazolyl)ethoxy)phenyl)2-thieathyl]1,2,4-triazolin-3-one.

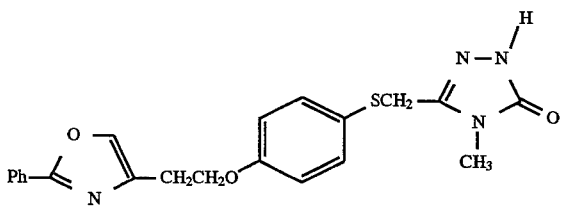

Part A

Preparation of: N,N-Dimethyl 4-[2-(2-phenyl-4-oxazolyl)ethoxy]phenylthionocarbamate.

A stirred mixture of 15.5 gm of the intermediate prepared as in Example 7 Part B and 50 mL DMF was treated with 2.8 gm of 60% NaH/oil. Gas evolution occurred and was allowed to proceed at autogenous temperature for 0.25 hours. The resulting dark mixture was treated with 7.0 gm N,N-Dimethyl thiocarbamoyl chloride and stirred for 3 hours. The mixture was treated with ice and the thick curdy solid filtered. The solid was washed with $H_2O$, hexane and recrystallized from $CH_2Cl_2$-hexane (decolorizing carbon) to provide 18.3 gm (90%) of white flakes mp 111°–113° C.

Anal.: Cal. for $C_{20}H_{20}N_2O_3S$: C, 65.20; H, 5.47; N, 7.60. Found: C, 65.26; H, 5.50; N, 7.59. MS: m/e 368.

Part B

Preparation of: N,N-Dimethyl 4-[2-(2-phenyl-4-oxazolyl)ethoxy]phenylthiolcarbamate.

A stirred mixture of 4.15 gm of the intermediate from Example 8 Part A and 15 mL of tetraglyme was heated to reflux for a total of 17 hours and cooled. The dark solid mass was treated with hexane, heated to boiling, cooled and filtered. The tan flakes were washed thoroughly with hexane and dried to provide 3.68 gm (88%), mp 128°–132° C.

Anal.: Cal. for $C_{20}H_{20}N_2O_3S$: C, 65.20; H, 5.47; N, 7.60. Found: C, 64.97; H, 5.50; N, 7.52.

Part C

Preparation of: Methyl S-4-[2-(2-phenyl-4-oxazolyl)ethoxy]phenylthioglycolic acid hydrazide.

A stirred mixture of 3.4 gm of the intermediate prepared in Example 8 Part B, 50 mL MeOH and 15 mL 2N NaOH was refluxed for 6 hours, cooled and acidified to pH4 with HOAc. The mixture was extracted with three 125 mL portions of EtOAc. The extracts were washed with $H_2O$, brine, dried over $MgSO_4$, filtered, and evaporated. The residual oil was dissolved in 30 mL of methyl ethyl ketone, the solution treated with 1.5 mL of methyl bromoacetate, 4,5 gm powdered $K_2CO_3$, 0.5 gm powdered KI and refluxed 2 hours. The cooled mixture was diluted with H20 and extracted with three 50 mL portions of EtOAC. The extracts were washed with $H_2O$, brine, dried over $MgSO_4$, filtered, and evaporated to provide 4.5 gm of a semi-solid oil. A solution of 2.7 gm of this oil in 25 mL MeOH was treated with 2 mL 85% hydrazine hydrate, 0.1 gm NaOMe and refluxed 1 hour. The solution was kept at room temperature overnight, diluted with $H_2O$ and the resulting precipitate filtered. The solid was washed with $H_2O$, dried and recrystallized from i-PrOH-hexane to provide 2.93 gm (69% overall) of nearly white powder mp 118°–121° C.

Anal.: Cal. for $C_{19}H_{19}N_3O_3S$: C, 61.77; H, 5.18; N, 11.37. Found: C, 61.71; H, 5.20; N, 11.18. MS: m/e 369.

Part D

A stirred suspension of 1.2 gm of the intermediate from Example 8, Part C in 20 mL THF was treated with 1 mL of methyl isocyanate and the resulting solution stirred at ambient temperature for 2 hours. The solvent was removed by evaporation and the residue dissolved in 25 mL MeOH. The solution was treated with 2.8 gm of 85% KOH and heated to reflux for 7 hours. The mixture was kept at room temperature overnight, heated just to boiling to redissolve a small amount of solid and acidified with 5N HCl. The hot mixture was treated with ice, diluted with $H_2O$ and the resulting solid filtered. The solid was washed with $H_2O$ and recrystallized from i-PrOH-hexane to provide 0.47 gm (35%) of 4-methyl-5-[(2-(2-phenyl-4-oxazolyl) ethoxyphenyl)2-thiaethyl]1,2,4-triazolin-3-one mp 130°–132° C.

Anal.: Cal. for $C_{21}H_{20}N_4O_3S$: C, 61.75; H, 4.94; N, 13.72. Found: C, 61.99; H, 5.00; N, 13.42. MS: m/e 408. IR: 1725 1577 cm$^{-1}$. NMR: delta 3.1 (t, 2H), 3.3 (s, 3H), 3.8 (s, 2H), 4.3 (t, 2H), 6.9 (d, 2H), 7.2 (d, 2H), 7.5 (m, 4H), 7.8 (s, 1H), 8.7 (broad s, 1H, exchanges with $D_2O$).

Example 8A

This Example prepares a compound outside the scope of the invention (contrast to compound prepared in Example 8, supra.).

13

Preparation of: 4-Methyl-5-[4-((2-(2-phenyl-4-oxazolyl)ethoxy)phenyl)-1-thiaethyl]1,2,4-triazolin-3-thione

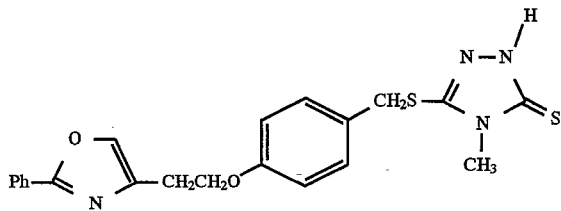

Part A:

Preparation of: Methyl 4-[2-(2-phenyl-4-oxazolyl)-ethoxy]benzoate.

A stirred solution of 14.2 g 2-(2-phenyl-4-oxazolyl)ethanol), 11.45 g methyl 4-hydroxybenzoate, 19.67 g triphenylphosphine and 150 mL THF was treated dropwise with diethyl azodicarboxylate (11.8 mL) over 0.5 hours allowing the temperature to rise spontaneously to 50°–60° C. The reaction mixture was stirred at ambient temperature 24 hours, treated with 3 mL of 30% $H_2O_2$ and evaporated in vacuo. The residue was dissolved in 250 mL EtOAc, the solution was successively treated with 2N NaOH, $H_2O$, brine, dried over $MgSO_4$, and filtered. After removal of the solvent the residue was chromatographed over silica. The product was recrystallized from THF/hexane to provide 23.66 g (97%) of white flakes mp 100°–102° C.

Anal.: Cal. for $C_{19}H_{17}NO_4$: C, 70.58; H, 5.30; N, 4.33. Found: C, 70.83; H, 5.33; N, 4.49.IR: 1707 cm$^{-1}$. (t, 2HO), 6.9 (d, 2 h), 7.5 (m, 4H), 7.8 (s, 1 h), 8.0 (m, 3H).

Part B:

Preparation of: 4-[2-(2-Phenyl-4-oxazolyl)-ethoxy]phenylmethanol.

A solution of 4.4 g of the intermediate prepared as in Example 8A, Part A in 50 mL THF was added dropwise to a stirred suspension of 2.7 g LiAlH$_4$ in 50 mL THF over 1 hour. The mixture was stirred an additional 1 hour and treated dropwise with 2 mL $H_2O$/8 mL THF, 4 mL % N NaOH, 8 mL $H_2O$, stirred and filtered. The white powder was washed with THF. The combined filtrate and washings were dried with $K_2CO_3$ and the solvent evaporated to provide an oil which solidified on scratching. Recrystallization from THF-hexane produced 4.02 g (98%) of fluffy powder mp 96°–99° C.

Anal.: Cal. for $C_{18}H_{17}NO_3$: C, 73.20; H, 5.80; N, 4.74. Found: C, 73.01; H, 5.82; N, 4.51. IR: 3526, 2881 cm$^{-1}$. MS: m/e 295.

Part C

A stirred mixture of 1.40 g of the intermediate prepared as in Example 8A, Part B, 1.30 g 1-methyl-1,3,4-triazole-2,5-dithione and 30 mL i-PrOH was treated with 2.4 mL 48% HBr and heated to reflux for 3 hours. The cooled mixture was diluted with $H_2O$ and filtered. The resulting white powder was washed with $H_2O$ and filtered. The resulting white powder was washed with $H_2O$ and recrystallized from THF/i-PrOH to provide 1.65 g (82%) of 4-Methyl-5-[4-((2-(2-phenyl-4-oxazolyl)ethoxy)phenyl)-1-thiaethyl]1,2,4-triazolin-3-thione mp173°–175° C. as fluffy white needles.

Anal.: Cal. for $C_{21}H_{20}N_4O_2S_2$: C, 59.41; H, 4.75; N, 13.20; S, 15.10. Found: C, 59.59; H, 4.80; N, 13.22; S, 14.81. MS: m/e 424. NMR: (DMSO-d$_6$): delta 3.1 (t, 2H), 3.35 (s, 3H), 4.3 (t, 2H), 4.35 (s, 2H), 6.9 (d, 2H), 7.2 (d, 2H), 7.5 (m, 3H), 7.6 (s, 1H), 8.0 (m, 2H).

Example 9

Preparation of: 4-Methyl-5-((2-(2-phenyl-4-oxazolyl)ethoxy)phenyl)-2-ethyl]1,2,4-triazolin-3-one.

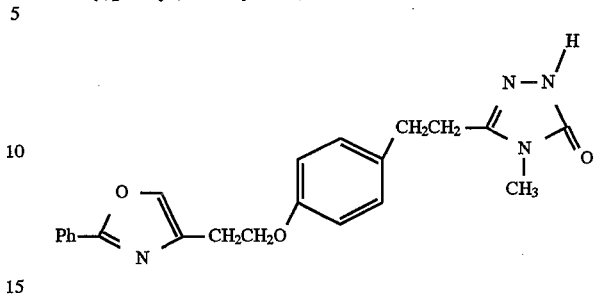

Part A

Preparation of: 4-[2-(2-Phenyl-4-oxazolyl)ethoxy]phenyl-3-propanoic acid hydrazide.

A stirred solution of 15.15 gm 2-(2-phenyl-4-oxazolyl)ethanol), 14.42 gm methyl 4-hydroxydihydrocinnamate, 20.98 gm triphenyl phosphine and 200 mL anhydrous THF was treated dropwise with 12.6 mL diethyl azodicarboxylate over 15 minutes, allowing the temperature to rise spontaneously to 50°–60° C. The solution was stirred at ambient temperature for 48 hours, treated with 2 mL 30% $H_2O_2$ and evaporated in vacuo. The residue was dissolved in 250 mL of EtOAC and the solution washed successively with 2N NaOH, $H_2O$, brine and dried over $MgSO_4$. After removal of solvent the residue was chromatographed over silica to provide 21.93 gm (78%) of ester mp 47°–48° C. A solution of 3.51 gm of ester in 25 mL of MeOH was treated with 4 mL 85% hydrazine hydrate, 0.1 gm NaOMe and refluxed 2 hours. The cooled mixture was diluted with $H_2O$ and the solid filtered. The solid was washed with $H_2O$ and dried to provide 3.4 gm (97%) of product mp 144°–145° C.

Anal.: Cal. for $C_{20}H_{21}N_3O_3$: C, 68.36; H, 6.02; N, 11.96. Found: C, 68.40; H, 6.06; N, 11.84. MS: m/e 351.

Part B

A sample of 4.04 gm of the hydrazide prepared in Example 9 Part A was suspended in 40 mL THF and treated with 0.6 mL of methyl isocyanate. The mixture was refluxed 1 hour, cooled, diluted with Et$_2$O and filtered. The white solid (3.5 gm, mp 166°–168° C.) was added to a solution prepared from 1.6 gm of Na metal and 25 mL of MeOH and the resulting solution refluxed for 6 hours. The cooled solution was acidified with 2N HCl and the resulting white solid filtered, washed with $H_2O$ and dried. Recrystallization from i-PrOH provided 1.7 gm (50%) of 4-methyl-5-[4-((2-(2-phenyl-4-oxazolyl)ethoxy)-phenyl)-2-ethyl]1,2,4-triazolin-3-one mp, 127°–129° C.

Anal.: Cal. for $C_{22}H_{24}N_4O_3$: C, 67.68; H, 5.68; N, 14.35. Found: C, 67.56; H, 5.69; N, 14.57. MS: m/e 390. NMR: delta 2.75 (t, 2H), 2.95 (t, 2H), 3.05 (s, 3H), 3.1 (t, 2H), 4.3 (t, 2H), 6.9 (d, 2H), 7.2 (d, 2H), 7.5 (m, 4H), 7.8 (s, 1H), 9.3 (broad s, 1H, exchanges with D$_2$O).

Example 9 A

This Example prepares a compound outside the scope of the invention (contrast to compound prepared in Example 9, supra.).

Preparation of: 4-Methyl-5-[4-(2-(2-phenyl-4-oxazolyl) ethoxy)phenyl]1,3,4-triazolin-3-thione.

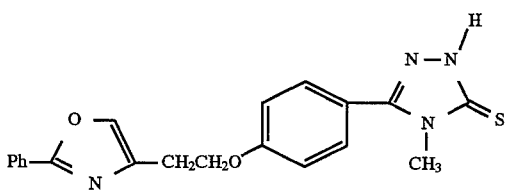

Part A:
Preparation of: 4-[2-(2-Phenyl-4-oxazolyl)ethoxy] benzoylhydrazine.

A stirred solution of 3.23 g of the intermediate prepared as in Example 8A, Pare A in 40 mL MeOH was treated with 5 mL of 80% hydrazine hydrate, 0.1 g NaOMe and heated to reflux for 3 hours. The cooled mixture was diluted with $H_2O$ and filtered. The white solid was washed with $H_2O$ and dried to provide 3.00 g (97%) of hydrazide mp 157°–159° C.
Part B
A stirred mixture of 1.89 g of the intermediate prepared as in Example 9A Part A in 40 mL THF was treated with 1.06 g methyl isothiocyanate and heated to reflux for 1 hour. the resulting solution was kept at room temperature 12 hours and evaporated in vacuo. The residue was boiled with EtOH, cooled and filtered. The white solid was washed with $Et_2O$ and added to a solution prepared from 0.64 g Na metal/25 mL MeOH. The resulting mixture was heated to reflux 3 hours, cooled and treated with 100 mL 2N HCl. The resulting precipitate was filtered, washed with $H_2O$ and recrystallized from THP/i-PrOH to provide 2.12 g (91%) of 4-Methyl-5-[4-(2-(2-phenyl-4-oxazolyl)ethoxy)phenyl]1,3, 4-triazolin- 3thione mp 188°–190° C.

Anal.: Cal. for $C_{20}H_{18}N_4O_2S$: C, 63.47; H, 4.79; N, 14.80. Found: C, 63.45; H, 4.88; N, 14.79. IR: 3120, 1610 $cm^{-1}$. MS: m/e 378. NMR: delta 3.1 (t 2H), 3.7 (s, 3H, 4.4 (t, 2H, 7.1 (d, 2H), 7.5 (m, 3H), 7.6 (d, 2H), 7.65 (s, 1H), 8.0 (m, 2H).

Example 10

Preparation of: 4-Methyl-5-[4-((2-(2-phenyl-4-oxazolyl) ethoxy)phenyl)-2-ethyl]1,2,4-triazolin-3-thione.

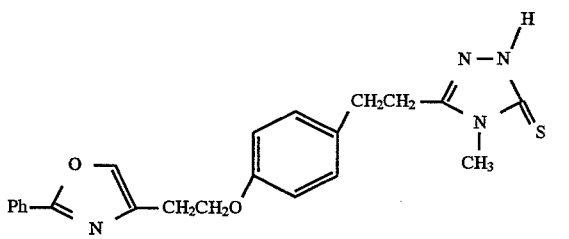

A suspension of 1.75 gm of the intermediate prepared as in Example 9 Part A and 25 mL THF was treated with 0.8 gm methyl isothiocyanate and refluxed 1 hour. The resulting solution was kept at room temperature 12 hours, and diluted with hexane. The resulting solid was filtered, washed with hexane and recrystallized from EtOH to give 1.34 gm of white powder mp 142°–144° C. This powder was added to a solution prepared from 0.7 gm Na metal and 20 mL MeOH and refluxed for 2 hours. The cooled solution was acidified with 2N HCl diluted with $H_2O$ and stirred at room temperature overnight. The solid was filtered, washed with $H_2O$, dried and recrystallized from THF-i-PrOH to provide 1.14 gm (56%) of 4-methyl-5-[4-((2-(2-phenyl-4-oxazolyl) ethoxy)phenyl)-2-ethyl]1,2,4-triazolin-3-thione mp 152°–154° C.

Anal.: Cal. for $C_{22}H_{22}N_4O_2S$: C, 65.00; H, 5.45; N, 13.78. Found: C, 64.71; H, 5.44; N, 13.65. MS: m/e 406. NMR: delta 2.75 (t, 2H), 2.9 (t, 2H), 3.0 (t, 2H), 3.1 (t, 2H), 3.4 (s, 3H), 4.9 (s, 1H, exchanges with $D_2O$), 6.9 (d, 2H), 7.2 (d, 2H), 7.5 (m, 4H), 7.8 (s, 1H).

Example 11

Preparation of: 5-[4-((2-(2-phenyl-4-oxazolyl)-ethoxy) phenyl)methyl]1,2,4-oxadiazolin-3-thione.

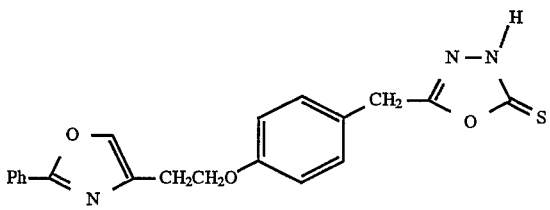

A stirred suspension of 3.37 gm of the intermediate prepared as in Example 1 Part B, 0.84 gm 85% KOH and 30 mL EtOH was treated with 0.6 mL $CS_2$ and heated to reflux 8 hours. The mixture was kept at room temperature overnight, the solvent evaporated in vacuo and the residue treated with 1N HCl. The white solid was filtered, washed with $H_2O$ and dried. Chromatography over silica followed by several recrystallizations from THF-hexane provided 1.07 gm (28% of product mp 194°–197° C.

Anal.: Cal. for $C_{20}H_{17}N_3O_3S$: C, 63.31; H, 4.52; N, 11.07. Found: C, 63.60; H, 4.82; N, 1080. MS: m/e 379. IR: 1625 $cm^{-1}$. NMR: delta 3.1 (t, 2H), 4.05 (s, 2H), 4.3 (t, 2H), 6.9 (d, 2H), 7.2 (d, 2H), 7.5 (m, 4H), 7.8 (s, 1H).

Example 11A

This Example prepares a compound outside the scope of the invention (contrast to compound prepared in Example 11, supra.).
Preparation of: 5-[4-(2-(2-Phenyl-4-oxazolyl)-ethoxy] phenyl-1,3,4-oxadiazole-2-thione.

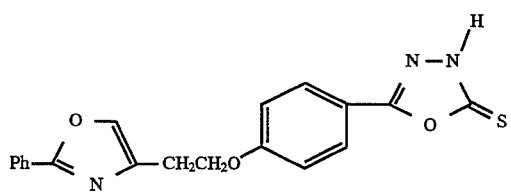

A stirred mixture of 4.05 g of the intermediate prepared as in Example 9A, Part A and 75 mL MeOH was treated with 1 mL carbon disulfide, 4.0 g of KOH and heated to reflux for 12 hours. An additional 1 mL carbon disulfide was added and refluxing continued for an additional 24 hours. The mixture was stirred at ambient temperature for 36 hours, neutralized with HOAc and concentrated. The residue was chromatographed to provide 1.73 g (38% of white powder mp 229°–231° C.).

Anal.: Cal. for $C_{19}H_{15}N_3O_3S$: C, 62.45; H, 4.12; N, 11.50. Found: C, 62.66; H, 4.41; N, 11.23. IR: 2878, 1614 $cm^{-1}$. MS: m/e 365. NMR: delta 3.1 (t, 2H), 3.4 (broad s, 1H, exchanges with $D_2O$), 4.4 (t, 2HO, 7.15 (d, 2H), 7.5 (m, 3H), 7.8 (d, 2H), 8.0 (m, 2H), 8.1 (s, 1H).

Example 12

Preparation of: 5-[(4-(2-(2-Phenyl-4-oxazolyl)ethoxy)phenyl)methyl]1,2,4-triazolin-3-one.

Part A
Preparation of:

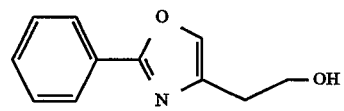

To an ice-cooled suspension of 5.87 g (0.155 mol) of LiAlH₄ in 700 mL of Et₂O was added a solution of 35.53 g (0.154 mol) of ethyl 2-phenyl-4-oxazoleacetate in 300 mL of Et₂O over a 1.5 hour period. The temperature of the reaction during the addition was kept below 15° C. After stirring for 2 hours at 25° C. the reaction was decomposed by the addition of 15 mL of EtOAc and 33.5 mL of H₂O. The mixture was filtered through anhydrous Na₂SO₄ and concentrated in vacuo to leave 28.1 g of oil. Distillation of the crude oil gave 2-(2-phenyl-4-oxazolyl)ethanol (23.52 g, 81%, bp 120°–122° C./0.05–0.06 mm) as an oil which solidified on standing. Elemental analysis for $C_{11}H_{11}NO_2$, Calcd.: C, 69.83; H, 5.86; N, 7.40. Found: C, 69.78; H, 5.90; N, 7.49.

Part B
Preparation of:

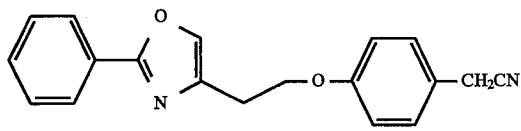

To a solution of 5.15 g (0.0272 mol) of product of Example 12 Part A, 4.83 g (0.0363 mol) p-hydroxybenzyl nitrile and 8.20 g (0.0313 mol) triphenylphosphine in 85 mL of freshly distilled THF at 0° C. was added 4.70 mL diethyl azodicarboxylate over a 15 minute period. The reaction mixture was stirred at 25° C. for 16 hours and then treated with 1.5 mL of 30% H₂O₂ followed by 100 mL of Et₂O. The organic layer was washed successively with 1N NaOH and H₂O. After drying over anhydrous Na₂SO₄ and filtering the solvent was removed. Addition of Et₂O precipitated triphenylphosphine oxide which was removed by filtration. The residue after removal of the solvent was chromatographed on silica. Elution with CH₂Cl₂ gave 4-[2-(2-phenyloxazolyl)ethoxy]phenyl-acetonitrile (5.46 g, 66% , mp 81°–83° C.

Elemental analysis for $C_{19}H_{16}N_2O_2$, Calcd.: C, 74.98; H, 5.30; N, 9.20. Found: C, 75.08; H, 5.38; N, 8.98.

Part C
Preparation of:

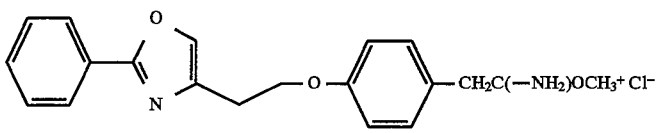

Method 1:

A solution of 1.0 g (3.29 mmol) of product of Example 12 Part B and 0.146 mL of anhydrous MeOH in 10 mL of CH₂Cl₂ at 0° C. was saturated with gaseous HCl and kept for 20 hours in the cold. The reaction mixture was evaporated to dryness in vacuo to leave 1.2 g of 4-[2-(2-phenyl-4-oxazolyl)ethoxy]benzeneethanimidic acid methyl ester hydrochloride as a white solid, mp 182°–184° C.

NMR (CDCl₃): delta 3.327 (t, 2H), 4.000 (s, 2H), 4.257 (s, 3H), 4.387 (t, 2H), 6.911 (d, 2H), 7.359 (d, 2H), 7.543–7.649 (m, 3H), 7.759 (s, 1H), 8.329 (d, 2H), 11.790 (br.s, 1H), 12.783 (br.s., 1H).

Method 2:

A stirred mixture of 7.8 g of nitrile from Example 12 Part B and 80 mL of MeOH was cooled to 0° C. and gaseous HCl was introduced for 1 hour until dissolution occurred. Anhydrous Et₂O (700 mL) was added and the resultant oil was washed with Et₂O and solidified on standing leaving crude 4-[2-(2-phenyl-4-oxazolyl)ethoxy]-benzeneethanimidic acid methyl ester hydrochloride.

Part D
Preparation of Example 12:

A mixture of 5.8 g of iminoether product of Example 12 Part C Method 1, 1.75 g of semicarbazide HCl, 100 mL of Py (pyridine) and 100 mL of DMF (dimethyl formamide) was refluxed for 5 hours. After cooling, H₂O was added and the mixture was evaporated in vacuo and crystallized from a mixture of MeOH-H₂O and washed with CH₂Cl₂ leaving 1.21 g of 5-[(4-(2-(2-phenyl-4-oxazolyl)ethoxy)phenyl)methyl]-1,2,4-triazolin-3-one as a white solid (20%, mp 222°–229° C.).

Elemental analysis for $C_{20}H_{18}N_4O_3$, Calcd.: C, 66.29; H, 5.01; N, 15.46. Found: C, 66.14; H, 5.11; N, 15.41. FD-MS m/e 362; NMR (DHSO-d6): delta 2.944 (t, 2H), 3.585 (s, 2H), 4.195 (t, 2H), 6.870 (d, 2H), 7.113 (d, 2H), 7.464–7.482 (m, 3H), 7.898–7.928 (m, 2H), 7.983 (s, 1H), 11.104 (s, 1H), 11.198 (s, 1H).

Example 13

Preparation of: 5-[(4-(2-(2-Phenyl-4-oxazolyl)ethoxy)phenyl)methyl]2,3,4-oxadiazolin-2-one.

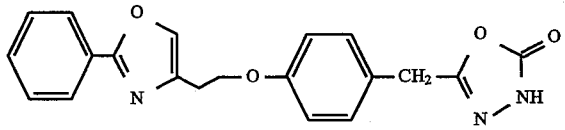

A solution of 1.4 mL of phenyl chloroformate in 20 mL of CH₂Cl₂ was added to a stirred mixture of 3.45 g of hydrazide from Example 1 Part B, 1.5 mL of Py and 800 ml of CH₂Cl₂ at 15° C. After stirring for two days at 25° C., 630 mL of solvent was removed and the mixture was stirred for another

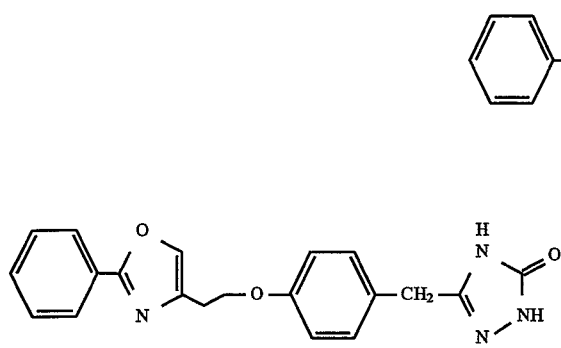

five days. Methylene chloride was added to bring the total volume to 500 mL and the reaction was washed successively with aqueous NaHCO₃, aqueous 5% citric acid, H₂O and dried over anhydrous Na₂SO₄. Evaporation of the solvent after filtration left 4.9 g of residue which was chromatographed on 120 g of silica. Elution with 1–2% MeOH in CH₂Cl₂ gave 1.9 g of a mixture of intermediate phenoxycarbonyl hydrazide and product 1,3,4-oxadiazol-2-one. Further elution with 3% MeOH in CH₂Cl₂ provided 1.3 g of recovered starting hydrazide.

The 1.9 g of the above mixture was dissolved in 175 mL of EtOH and treated with 30 ml of 1N HaOH for 2.5 hours at 25° C. After acidification with aqueous HCl, the solvent was removed and the residue was dissolved in CHCl₃, washed with H₂O and brine and dried over anhydrous Na₂SO₄. Removal of the solvent left 2.0 g of white solid which was recrystallized from 50 mL of MeOH to give 1.3 g of 5-[(4-(2-(2-phenyl-4-oxazolyl)-ethoxy)phenyl)methyl] 1,3,4-oxadiazolin-2-one (56%, mp 142°–144° C.).

Elemental analysis for C₂₀H₁₇N3O₄, Calcd.: C, 66.11, H, 4.72, N, 11.56. Found: C, 65.84, H, 4.90, N, 11.34. FD-MS: m/e 363; NMR DMSO-d6): delta (t, 2H), 3.799 (s, 2H), 4.209 (t, 2H), 6.903 (d, 2H), 7.155 (d, 2H), 7.463–7.483 (m, 3H), 7.905–7.931 m, 2H), 7.988 (s, 1H), 12.072 (br.s, 1H).

Example 14

Preparation of: 3-[(4-(2-(2-Phenyl-4-oxazolyl)ethoxy) phenyl)methyl]1,2,4-oxadiazolin-5-one.

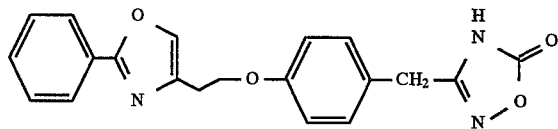

Part A
Preparation of:

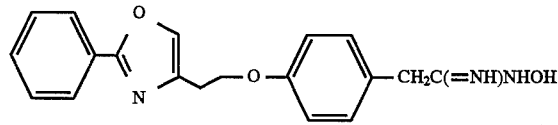

To a cooled (0° C.) solution of 0.88 g of Na in 80 mL of anhydrous MeOH was added 2.67 g of NH₂OH HCl followed by a solution of the iminoether of Example 12 Part C Method 2 in 100 mL of anhydrous MeOH. The reaction mixture was allowed to warm to 25° C. and was stirred for 18 hours. The residue, after removal of solvent, was partitioned between 200 mL of H₂O and 700 mL of EtOAc. The solid was removed by filtration and washed with H₂O and EtOAc. The combined organic phases were washed with H₂O and combined with the solid. After removal of the solvent, the residue was recrystallized from MeOH. The filtrate was diluted with Et₂O and the resulting solid was filtered to give 4.14 g of crude N-hydroxy-4-[2-(2-phenyl-4-oxazolyl)ethoxy]benzeneethanimidamide. FD-MS: m/e 337.

Part B
Preparation of Example 14:

A mixture of 4.06 g of the amidoxime from Example 14 Part A, 150 mL of THF and 1.98 g of carbonyldiimidazole was heated at reflux for 7 hours, cooled to 25° C., and stirred another 16 hours. The solvent was removed in vacuo. The residue was dissolved in 600 mL of EtOAc, washed with H₂O and dried over anhydrous Na₂SO4. The residue, obtained after filtration and evaporation of the solvent, was recrystallized from EtOH to give 3.11 g of 3-[(4-(2-(2-phenyl-4-oxazolyl)ethoxy)phenyl)-methyl]1,2,4-oxadiazolin-5-one, (71% mp 154.5°–157.5° C.).

Elemental analysis for C₂₀H₁₇N₃O₄, Calcd C.: C, 66.11; H, 4.72; N, 11.56. Found: C, 66.32; H, 4.77; N, 11.34. NMR (DMSO-d6): delta (t, 2H), 3.747 (s, 2H), 4.210 (t, 2H), 6.906 (d, 2H), 7.167 (d, 2H), 7.464–7.483 (m, 3H), 7.905–7.929 (m, 2H), 7.988 (s, 1H), 12.232 (br.s, 1H).

Example 15

Preparation of: 5-[(4-(2-(2-phenyl-4-oxazolyl)ethoxy) phenyl)methyl]1,3,4-oxathiazolin-2-one

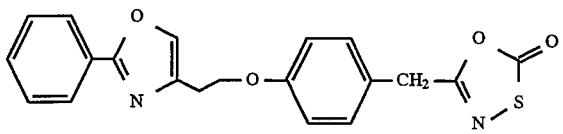

Part A
Preparation of:

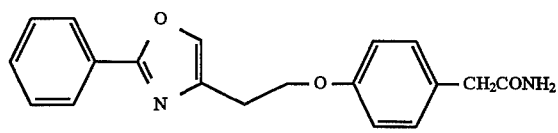

A solution of 0.5 g of methyl ester of Example 1 Part A, 50 mL of MeOH, 0.2 g of NH₄Cl and 40 mL of NH₄OH was stirred at 25° C. for 48 hours with brief, intermittent warming at 50° C. The MeOH was partially removed, and the reaction mixture was diluted with H₂O. The solid precipitate was filtered, washed with H₂O and dried to give 4-(2-(2-phenyl-4-oxazolyl)ethoxy)phenylacetamide (0.39 g, 82%, mp 180°–183.5° C.).

Elemental analysis for C₁₉H₁₈N₂O₃, Calcd.: C, 70.79; H, 5.63; N, 8.69. Found: C, 70.54; H, 5.72; N, 8.50. FD-MS: m/e 322; NMR (DMSO-d6): delta 2.968 (t, 2H), 3.250 (s, 2H), 4.214 (t, 2H), 6.788 (br.s, 1H), 6.865 (d, 2H), 7.350 (d, 2H), 7.354 (br.s, 1H), 7.493–7.504 (m, 3H), 7.928–7.954 (m, 2H), 8.008 (s, 1H).

Part B
Preparation of Example 15:

To a stirred mixture of 3.6 g of amide of Example 15 Part A and 200 mL of toluene at 82° C. was added dropwise 1.05 mL of chlorocarbonylsulfenyl chloride. The reaction was heated for 7 hours at 82° C. and stirred an additional 18 hours at 25° C. The volatiles were removed in vacuo, and the residue was partitioned between CHCl₃ and H₂O. The layers were separated and the aqueous layer was extracted with CHCl₃. The combined organic layers were evaporated and chromatographed on 57 g of silica. Elution with 0.5% MeOH in CH₂Cl₂ gave 1.7 g solid which was recrystallized from a mixture of acetone and Et₂O to give 1.4 g of 5-[(4-(2-(2-phenyl-4-oxazolyl)-ethoxy)phenyl)methyl]1,3, 4-oxathiazolin-2-one (29%, mp 103°–105° C.).

Elemental analysis for C₂₀H₁₆N₂O₄S, Calcd.: C, 63.15; H, 4.24; N, 7.36. Found: C, 63.01; H, 4.28; N, 7.31. FD-MS: m/e 380; NMR (CDCl₃): delta 2.962 (t, 2H), 3.938 (s, 2H), 4.223 (t, 2H), 6.918 (d, 2H), 7.203 (d, 2H), 7.459–7.503 (m, 3H), 7.909–7.938 (m, 2H), 7.998 (s, 1H).

Example 16

Preparation of: 3-[(4-(2-(2-phenyl-4-oxazolyl)ethoxy)phenyl)methyl]1,2,4-thiadiazolin-5-one.

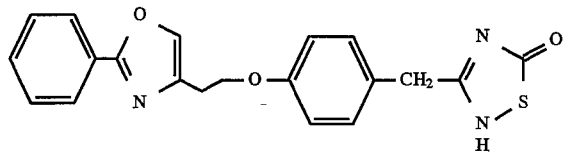

Part A
Preparation of:

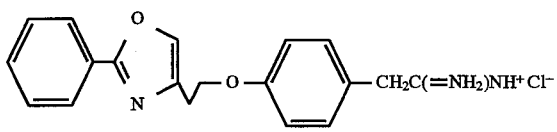

To a mixture of 4-(2-(2-phenyl-4-oxazolyl)ethoxy)benzene-ethanimidic acid methyl ester hydrochloride of Example 12 Part C, obtained from 20.0 g of nitrile Example 12 Part B, 3.6 g of $NH_4Cl$ and 200 mL of anhydrous MeOH was added 100 mL of anhydrous $NH_4OH$ saturated with $NH_3$. The reaction mixture was stoppered and stirred at 25° C. for 16 hours. The volatiles were removed in vacuo and the solid was treated with $H_2O$ and with MeCN and dried to leave 21.4 g of 4-(2-(2-phenyl-4-oxazolyl)ethoxy)benzeneethanimidamide hydrochloride, mp 187°–194° C. 4.94 g portion of solid was dissolved in 50 mL of refluxing MeOH, filtered, and diluted with 80 mL of MeCN. Most of the MeOH was evaporated and the solution was cooled and allowed to crystallize. Filtration gave 4.45 g of 4-(2-(2-phenyl-4-oxazolyl)ethoxy)benzeneethanimidamide hydrochloride as a white solid after washing with $Et_2O$, mp 191°–193° C.

Elemental analysis for $C_{19}H_{19}N_3O_2$, Calcd.: C, 63.77; H, 5.63; N, 11.74. Found: C, 63.49; H, 5.72; N, 11.71.

Part B
Preparation of Example 16:

To a stirred suspension of 1.9 g of 60% NaH in mineral oil and 440 mL of freshly distilled THF was added 17.0 g of solid crude imidamide hydrochloride of Example 16 Part A. The mixture was stirred for 2.5 hours at 25° C. and 25.0 g of diisopropylethyl amine was added followed by 3.70 mL of chlorocarbonylsulfenyl chloride. After stirring for 18 hours, the reaction mixture was poured into $H_2O$ and extracted with EtOAc. The EtOAc layer was washed with $H_2O$, brine and dried over anhydrous $Na_2SO_4$. After filtration and evaporation of the solvent, the dark oil was chromatographed on 220 g of silica. Elution with 1% MeOH in $CH_2Cl_2$ afforded 8.2 g of solid which was recrystallized twice from a mixture of $CH_2Cl_2$ and hexanes to give 7.40 g of 3-[(4-(2-(2-phenyl-4-oxazolyl)ethoxy)phenyl)-methyl]1,2,4-thiadiazolin-5-one (41% mp 160°–163° C.).

Elemental analysis for $C_{20}H_{17}N_3O_3S$, Calcd.: C, 63.31, H, 4.52, N, 11.07. Found: C, 63.10; H, 4.61; N, 11.07. FD-MS: m/e 379; NMR (DMSO-d6): delta 2.991 (t, 2H), 3.746 (9s, 2H), 4.223 (t, 2H), 6.908 (d, 2H), 7.172 (d, 2H), 7.924–7.967 (m, 3H), 8.002 (s, 1H), 12.823 (br.s., 1H).

Example 17

Preparation of: 1-[(4-(2-(2-Phenyl-4-oxazolyl)ethoxy)phenyl)methyl]1,2,4-triazolidin-3,5-dione.

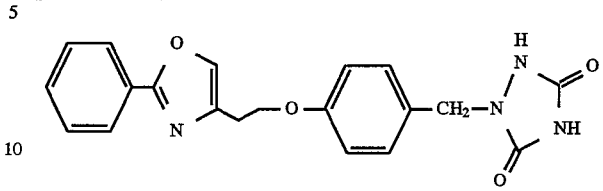

Part A
Preparation of:

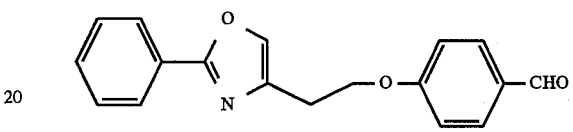

To a solution of 72.7 g of alcohol product of Example 9A, Part A, 47.9 of 4-hydroxybenzaldehyde, 104 g triphenylphosphine and 450 mL of anhydrous THF at –5° C. was added 75 g of diethyl azodicarboxylate over a 20 minute period. The temperature was maintained at 0° C. The cooling bath was removed and the reaction mixture was stirred for 20 hours at 25° C. After the addition of 5 mL of 30% $H_2O_2$ the reaction mixture was diluted with 1.2 L of $Et_2O$, washed with 1N NaOH and $H_2O$ and dried over $Na_2SO_4$. The solvent was removed and the residue was dissolved in 1 L of $Et_2O$ and cooled to 0° C. The solid which precipitated ($Ph_3PO$) was removed by filtration and the filtrate was concentrated to 600 mL and cooled to 0° C. The precipitate was filtered and recrystallized twice from acetone/$H_2O$ to give 4-(2-(2-phenyl-4-oxazolyl)ethoxy)-benzaldehyde (28.9 g, mp 92°–97° C.). An additional 32.6 of product (total yield 61.5 g, 54%) was obtained from filtrates.

Elemental analysis for $C_{18}H_{15}NO_3$, Calcd.: C, 73.71; H, 5.15; N, 4.77. Found: C, 73.84; H, 5.34; N, 5.02. FD-MS: m/e 293. NMR (DMSO-d6): delta 3.006 (t, 2H), 4.354 (t, 2H), 7.120 (d, 2H), 7.453–7.485 (m.3H), 7.817 (d, 2H), 7.902–7.932 (m, 2H), 8.018 (s, 1H), 9.820 (s, 1H).

Part B:

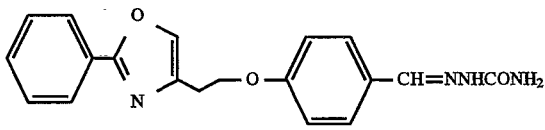

A mixture of 20.0 g of aldehyde from Example 17 Part A, 8.29 g of semicarbazide hydrochloride, 8.14 g of NaOAc and 150 mL of $H_2O$ was heated for 0.75 hours at 100° C. with occasional swirling. The heterogenous mixture was diluted with 150 mL of MeOH and allowed to stand at 25° C. for 64 hours. The solid was filtered and washed with $H_2O$, refluxed with 500 mL of MeOH and filtered hot leaving 21.3 g of 4-(2-(2-phenyl-4-oxazolyl)ethoxy)benzaldehyde semicarbazone (89%, m.p. 221°–226° C.).

Elemental analysis for $C_{19}H_{18}N_4O_3$, Calcd.: C, 65.13; H, 5.18; N, 15,99. Found: C, 64.91; H, 5.20; N, 15.73.

Part C
Preparation of:

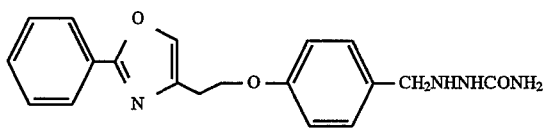

A mixture of 26.1 g of semicarbazone of Example 17 Part B in 500 mL of THF was treated with 298 mL of a 1N BH$_3$ in THF solution. After stirring for 14 hours at 25° C. the solution was slowly poured into 600 mL of MeOH. The reaction mixture was evaporated in vacuo to dryness. The solid was treated twice with 600 mL of MeOH by refluxing and evaporating the volatiles. The residue was then diluted with 400 mL of MeOH, cooled to 0° C. and filtered leaving 22.4 g N$^1$-[4-(2-(2-phenyl-4-oxazolyl)ethoxy)phenyl]methylsemicarbazide (85%, mp 192°–196° C.).

Elemental analysis for $C_{19}H_{20}N_4O_3$, Calcd.: C, 64.76; H, 5.72; N, 15.90. Found: C, 64.58; H, 5.67; N, 15.64. NMR (DMSO-d6): delta 2.951 (t, 2H), 3.655 (d, 2H), 4.203 (t, 2H), 4.823 (br.s, 1H), 5.732 (br.s, 2H), 6.856 (d, 2H), 7.207 (d, 2H), 7.468–7.485 (m, 3H), 7.902–7.932 (m, 2H), 7.993 (s, 1H).

Part D
Preparation of Example 17:

A mixture of 11.9 g of semicarbazide from Example 17 Part C, 8.10 g of carbonyldiimidazole, 0.5 mL of triethylamine and 400 mL of anhydrous DMF was stirred at 25° C. for 4 days, diluted with 1 L of H$_2$O and filtered. The filtrate was evaporated. The residue was treated with 100 mL of MeOH and the solid was filtered and dried to give 3.43 g of 1-[(4-(2-(2-phenyl-4-oxazolyl)ethoxy)phenyl)methyl]1,2,4-triazolidin-3,5-dione (27%. mp 223.5°–230° C.).

Elemental analysis for $C_{20}H_{18}N_4$, Calcd.: C, 63.49; H, 4.80; N, 14.81. Found: C, 63.24; H, 4.87; N, 14.80. FD-MS: m/e 378; NMR (DMSO-d6): delta 2.975 (t,2H), 4.235 (t, 2H), 4.418 (s, 2H), 6.928 (d, 2 h), 7.151 (d, 2hO, 7.488–7.504 (m, 3H), 7.926–7.951 (m, 2H), 10.2 (br.s, 1H), 10.9 (br.s, 1H).

Example 18

Preparation of: 1-[(4-(2-(2-Phenyl-4-oxazolyl)ethoxy)phenyl)methyl]1,3-diazolidin-2,4,5-trione.

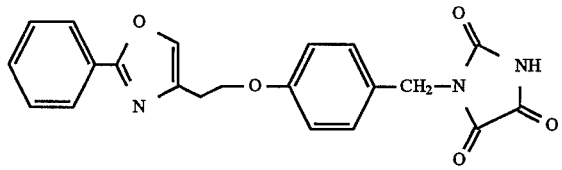

Part A
Preparation of:

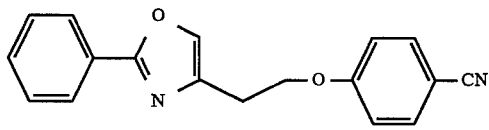

To a 12.89 g of 60% dispersion of NaH in mineral oil, washed three times with hexanes, was added 100 mL of anhydrous DMF. The stirred suspension was cooled to 10° C. and a solution of 52.1 g of alcohol from Example 9A Part A in 150 mL of anhydrous DMF was added dropwise. One hour after the completion of the addition, a solution of 37.59 g of parafluoro-benzonitrile in 100 mL of anhydrous DMF (dimethylformamide) was added slowly while keeping the reaction mixture at 15°–20° C. The reaction temperature was increased to 40° C. while the mixture stirred for 4 hours. After the third hour, an additional 1.05 g of 60% NaH dispersion was added. The reaction was allowed to stay at 25° C. for 16 hours and was then diluted slowly with 880 mL of H$_2$O. The precipitate which formed was filtered, washed with 1 L of H$_2$O followed by 1 L of hexanes and dried to give 71.8 g of 4-(2-(2-phenyl-4-oxazolyl)ethoxy)benzonitrile (90%, mp 114.6°–115° C.).

Part B
Preparation of:

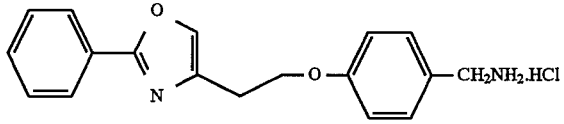

A solution of 12.34 g of nitrile from Example 18 Part A in 80 mL of anhydrous THF was added to a stirred suspension of 1.70 g of lithium aluminum hydride in 110 mL of anhydrous THF cooled to 10° C. over a 5 min period. Stirring at 10°C. was continued for 1.5 hours and then at 25° C. for 20 hours. The reaction mixture was decomposed by the sequential addition of 1.8 mL of H$_2$O, 1.3 mL of 5N NaOH and 6.3 ml of H$_2$O. The slurry was filtered and the solid was washed with THF. The combined filtrates were evaporated and the residue was dissolved in 500 mL of EtOAc. The solution was washed with H$_2$O and brine, dried over anhydrous Na$_2$SO$_4$, and filtered. Evaporation of the solvent left 12.4 g of amine which was taken up in MeOH and converted to the HCl salt by treatment with a solution of HCl in Et$_2$O. The residue, after evaporation of the volatiles, was crystallized from a mixture of 60 mL of MeOH and 350 mL of EtOAc. After filtration, the solid was washed with EtOAc and dried to give 11.4 g of 4-[(2-(2-phenyl-4-oxazolyl)ethoxy)-benzene]methyl amine hydrochloride (90%, mp 198°–206° C.).

FD-MS: m/e 294; NMR (DMSO-d6): delta 2.963 (t, 2H), 3.879 (d, 2H), 4.239 (t, 2H), 6.958 (d, 2H), 7.360 (d, 2H), 7.468–7.488 (m, 3H), 7.905–7.930 (m, 2H), 7.997 (s, 1 h), 8.271 (br.s, 3H).

Part C
Preparation of:

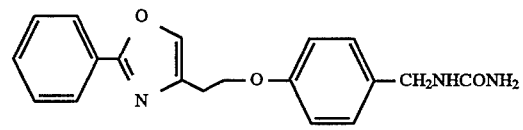

A mixture of 10.3 g of free amine of example 18 Part B, 120 mL of H$_2$O, 120 mL of MeOH and 7.0 mL of 5N HCl was stirred until the amine dissolved and 2.27 g of sodium cyanate was added. The reaction mixture was warmed to 50° C. and then allowed to cool to 25° C. After 2.5 hours, the mixture was cooled in an ice bath and filtered. The solid was washed with H$_2$O and recrystallized from 260 mL of EtOH and 350 mL of H$_2$O to give 6.05 g of N-4-(2-(2-phenyl-4-oxazolyl)ethoxy)-benzenemethyl urea (61% mp 191°–196° C.).

Elemental analysis for $C_{19}H_{19}N_3O_3$, Calcd.: C, 67.64; H, 5.68; N, 12.45. Found: C, 67.59; H, 5.75; N, 12.16. FD-MS: m/e 337; NMR (DHSO-d6): delta 2.946 (t, 2H), 4.040 (d, 2 h), 4.195 (t, 2H), 5.425 (s, 2H), 6.261 (t, 1H), 6.862 (d, 2H), 7.113 (d, 2HO, 7.464–7.485 (m, 3H), 7.902–7.932 (m, 2 h), 7.986 (s, 1H).

Part D

Preparation of Example 18:

To a solution of 0.38 g of Na in 100 mL of anhydrous MeOH at 0° C. was added 4.5 g of the substituted urea of Example 18 Part C. After several minutes of stirring, 2.0 mL of diethyl oxalate was added. The cooling bath was removed and the reaction mixture was stirred for four days. After the addition of 3 mL of 3N HCl and H$_2$O, the mixture filtered. The solid was washed with H$_2$O and recrystallized form 65 mL of THF and 75 mL of H$_2$O to give 3.28 g of 1-[(4-(2-(2-phenyl-4-oxazolyl)ethoxy)-phenyl)methyl]1,3-diazolidin-2,4,5,5-trione (63%, mp 217°–223° C.).

Elemental analysis for C$_{21}$H$_{17}$N$_3$O$_5$, Calcd.: C, 64.45; H, 4.38; N, 10.74. Found: C, 64.72; H, 4.52; N, 10.59. NMR (DHSO-d6): delta 2.946 (t, 2H), 4.216 (t, 2H), 4.510 (d, 2H), 6.882 (d, 2HO), 7.209 (d, 2H), 7.464–7.482 (m, 3H), 7.898–7.927 (m, 2H), 7.984 (s, 1H), 12.011 (s, 1H).

Example 19

Preparation of: 4-Isopropyl-5-[4-((2-(2-phenyl-4-oxazolyl)ethoxy)phenyl)methyl]1,2,4-triazolin-3-one.

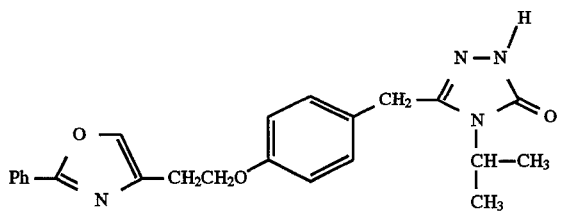

A suspension of 4.0 gm of the intermediate prepared as in Example 1 Part B was suspended in 30 mL of THF, treated with 1.3 g of iso-propyl isocyanate and refluxed for 2 hours. The mixture was cooled, diluted with Et$_2$O and filtered. The white solid (3.1 g) was collected, washed with Et$_2$O and added to a solution prepared from 4.19 gm of 85% KOH and 100 mL of MeOH. The resulting solution was heated to reflux for 7 days, at which time TLC showed complete consumption of starting material. The cooled solution was acidified with 1N HCl and the resulting precipitate collected by filtration. Purification was effected by sequential chromatography on silica gel columns, eluting with EtOAc and 30:1 CHCl$_3$/MeOH, respectively to provide 1.5 g (52%) of 4-isopropyl-5-[4-((2-(2-phenyl-4-oxazolyl)ethoxy)phenyl-4-oxazolyl)ethoxy)phenyl)methyl]1,2,4-triazolin-3-one as white needles, mp 140°–143° C.

Anal. Cal. for C$_{23}$H$_{24}$N$_4$O$_3$: C, 68.30; H, 5.98; N, 13.85. Found: C, 68.31; H, 6.10; N, 13.88. IR: 1685 cm$^{-1}$ MS: m/e 404. NMR: 1.3 (d, 2H), 3.09 (t, 2H), 3.84 (s, 2H , 4.01 (septet, 1H), 4.28 (t, 2H), 6.9 (d, 2H), 7.12 (m, 3H), 7.57 (s, 1H), 8.03 (m, 2H), 9.35 (s, 1H, exchanges with D$_2$O Example 20

Preparation of: 4-n-Propyl-5-[4-((2-(2-phenyl-4-oxazolyl)ethoxy)phenyl)methyl]1,2,4-triazolin-3-one.

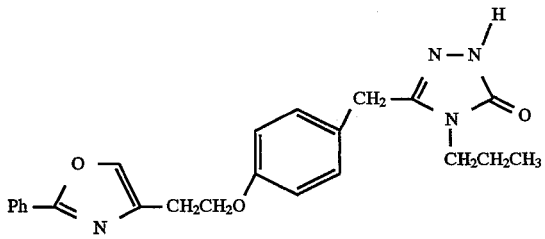

A suspension of 3.0 gm of the intermediate prepared as in Example 1 Part B was suspended in 30 mL of THF, treated with 1.01 g of n-propyl isocyanate and refluxed for 2 hours. The mixture was cooled, diluted with Et$_2$O and filtered. The white solid (3.3 g) was collected, washed with Et$_2$O and added to a solution prepared from 4.38 gm of 85% KOH and 100 mL of MeOH. The resulting solution was heated to reflux for 48 hours, at which time TLC showed complete consumption of starting material. The cooled solution was acidified with 1N HCl and the resulting precipitate collected by filtration. Purification was effected by chromatography on silica gel, eluting with CHCl$_3$ to provide 2.3 g (73%) of 4-n-propyl-5-[4-((2-(2-phenyl-4-oxazolyl)ethoxy)phenyl)methyl]1,2,4-triazolin-3-one as white needles, mp 131°–132° C.

Anal. Cal. for C$_{23}$H$_{24}$N$_4$O$_3$: C, 68.30; H, 5.98; N, 13.85. Found: C, 68.26; H, 6.13; N, 13.87. IR: 1694 cm$^{-1}$. MS: m/e 404. NMR: 0.72 (t, 3H), 1.31 (m, 2H), 3.0 (t, 2H), 3.34 (m, 4H), 3.84 (s, 2H), 4.25 (t, 2H), 6.92 (d, 2H), 7.17 (d, 2H), 7.54 (m, 3H), 7.97 (m, 2H), 8.02 (s, 1H), 11.45 (s, 1H), exchanges with D$_2$O).

Example 21

Preparation of: 2-Methyl-4-ethyl-5-[4-((2-(2-phenyl-4-oxazolyl)ethoxy)phenyl)methyl]1,2,4-triazolin-3-one.

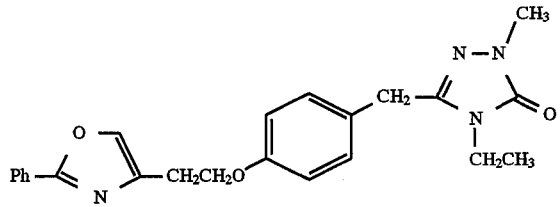

A stirred solution of 1.0 gm of the intermediate prepared in Example 2, Part A in 75 mL of DMF under N$_2$ was treated in one portion with 0.06 gm of 60% of NaH/oil and the resulting mixture allowed to react for 15 minutes. After addition of 0.54 gm of CH$_3$I, the mixture was kept at ambient temperature for 1 hour, poured onto ice and extracted with 100 mL EtOAc. The EtOAc solution was washed with H$_2$O, dried with Na$_2$SO$_4$ and evaporated. The solid residue was chromatographed over silica (elution with 2% MeOH in CHCl$_3$) to provide 0.7 gm (67%) of 2-methyl-4-ethyl-5-[4-((2-(2-phenyl-4-oxazolyl)ethoxy)phenyl)methyl]1,2,4-triazolin-3-one as colorless needles, mp 128°–130° C.

Anal.: Cal. for C$_{23}$H$_{24}$N$_4$O$_3$: C, 68.30; H, 5.98; N, 13.85. Found: C, 68.09; H,m 5.88; N, 14.00. Ms: m/e 404. IR: 1690 cm$^{-1}$. NMR: delta 1.0 (t, 3H), 3.07 (t, 2H), 3.25 (s, 3H), 3.3 (q, 2H), 4.26 (t, 2H), 6.88) d, 2 h), 7.12 (d, 2H), 7.43 (m, 3H), 7.55 (s, 1H), 8.02 (m, 2H).

Example 21A

This Example prepares a compound outside the scope of the invention (contrast to compound prepared in Example 21, supra.).

Preparation of: 4-Phenyl-5-[4-((2-(2-phenyl-4-oxazolyl)ethoxy)phenyl)methyl]1,2,4-triazolin-3-one.

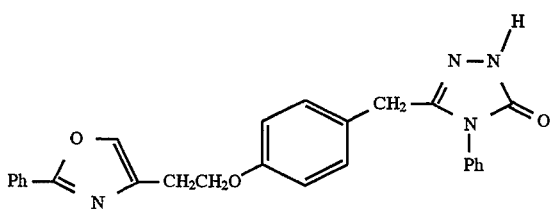

A suspension of 3.0 gm of the intermediate prepared as in Example 1 Part B was suspended in 30 mL of THF, treated with 1.4 g of phenyl isocyanate and refluxed for 2 hours. The mixture was cooled, diluted with Et$_2$O and filtered. The white solid (2.8 g) was collected, washed with Et$_2$O and added to a solution prepared from 3.87 gm of 85% KOH and 100 mL of MeOH. The resulting solution was heated to reflux for 7 days, at which time TLC showed complete consumption off starting material. The cooled solution was acidified with 1N HCl and the resulting precipitate collected by filtration. Purification was effected by recrystallization from MeOH to provide 1.3 g (43%) of product as white needles, mp 179°–181° C.

Anal. Cal. for C$_{26}$H$_{22}$N$_4$O$_3$: C, 71.22; H, 5.06; N, 12.78. Found: C, 71.11; H, 5.14; N, 12.97. IR: 1719 cm$^{-1}$. MS: m/e 438. NMR: 2.97 (t, 2H), 3.73 (s, 2H), 4.19 (t, 2H), 6.78 (d, 2 h), 6.85 (d, 2 h), 7.22 (dd, 2H), 7.44 (m, 3H), 7.53 (m, 3H), 7.97 (m, 2H), 8.02 (s, 1 h), 11.71 (s, 1H, exchanges with D$_2$O).

Testing Methods and Results

Compounds were tested for antihyperglycemic activity according to the protocol described in A. M. Gill and T. T. Yen, "Effects of Ciglitazone on Endogenous Plasma Islet Amyloid Polypeptide and insulin Sensitivity in Obese-Diabetic Viable Yellow Mice" Life Sciences 48, 703–710 (1991). The mice used in these tests were obese-diabetic viable yellow mice form the inbred Lilly colony. They were housed in transparent plastic cages with bedding. Purina Formula Chow 5008 (product of Purina Mills Inc., 717 South Hickory St., Fond Du Lac, Wis. 54935-5517 U.S.A.) and water were available ad libitum. The ambient temperature of the animal room was 25° C. and lights were on from 0600 to 1800.

To study the effects of the candidate compounds, twelve male obese-diabetic viable yellow (VY) mice were divided into two groups for each candidate compound. One group was fed mesh or repelletized Purina 5008 Chow and one group was fed the same chow (mammal food) containing the indicated amount of candidate compound as set forth below in the Table. Body weight and food consumption were monitored and blood samples collected before the experiment was initiated and after 14 days of treatment. In the Table, the blood glucose levels of mice given the test compounds are reported as a percentage of the initial value as compared to untreated controls on day 14 of treatment. Reductions of the initial values by less than 20% are regarded as inactive. The dose is the percent of compound incorporated into the feed (mesh or repelletized). The corresponding data for ciglitazone are included for comparison.

TABLE

| Example No. | Dose | BG % |
|---|---|---|
| 1 | .05 | 46% |
| 2 | .03 | 43% |
| 3 | .03 | 59 |
| 4 | .05 | 49.5% |
| 5 | .03 | 27.4% |
| 6 | .05 | 39.5% |
| 7 | .03 | 33% |
| 8 | .03 | 70.5% |
| 8A* | .03 | 97.6% |
| 9 | .03 | 55% |
| 9A* | .05 | 82% |
| 10 | .05 | 46.1% |
| 11 | .05 | 51% |
| 11A* | .05 | 109% |
| 12 | .03 | 43% |
| 13 | .03 | 40.7% |
| 14 | .05 | 34.7% |
| 15 | .03 | 40% |
| 16 | .03 | 47% |
| 17 | .05 | 41.8% |
| 18 | .03 | 57% |
| 19 | .03 | 54.4% |
| 20 | .03 | 28.2% |
| 21 | .03 | 53% |
| 21A* | .03 | 99.5% |
| Ciglitazone** | 0.1 | 64% |

*are comparative Examples to show criticality of structure
**control experiment

We claim:

1. A compound of the formula:

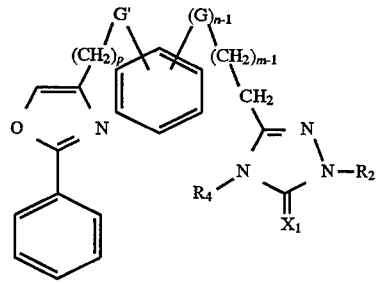

wherein G is O or S; G' is O or S; R$_2$ and R$_4$ are independently selected from the group consisting of H, methyl, ethyl, propyl, and butyl; X$_1$ is O or S, m is 1 or 2; n is 1 or 2; p is an integer from 1 to 6; or a pharmaceutically-acceptable salt thereof.

2. The compound of claim 1 wherein G' is O, p is 2, and the two bonds to the phenylene ring are at positions that are para to each other in the phenylene ring, or a pharmaceutically-acceptable salt thereof.

3. The compound of claim 2 wherein R$_2$ is H, or a pharmaceutically-acceptable salt thereof.

4. A compound selected from the group consisting of:
5-[4-((2-(2-phenyl-4-oxazolyl)ethoxy)phenyl)methyl]-1,2,4-triazolin-3-one;
5-[4-((2-(2-phenyl-4-oxazolyl)ethoxy)phenyl)methyl]-1,2,4-triazolin-3-thione;
4-methyl-5-[4-((2-(2-phenyl-4-oxazolyl)ethoxy)phenyl)methyl]-1,2,4-triazolin-3-one;
4-methyl-5-[4-((2-(2-phenyl-4-oxazolyl)ethoxy)phenyl)methyl]-1,2,4-triazolin-3-thione;
4-ethyl-5-[4-((2-(2-phenyl-4-oxazolyl)ethoxy)phenyl)methyl]-1,2,4-triazolin-3-one;
4-ethyl-5-[4-((2-(2-phenyl-4-oxazolyl)ethoxy)phenyl)methyl]-1,2,4-triazolin-3-thione;

5-[4-((2-(2-phenyl-4-oxazolyl)ethoxy)phenyl)oxymethyl]-1,2,4-triazolin-3-one;

5-[4-((2-(2-phenyl-4-oxazolyl)ethoxy)phenyl)oxymethyl]-1,2,4-triazolin-3-thione;

4-methyl-5-[4-((2-(2-phenyl-4-oxazolyl)ethoxy)phenyl)oxymethyl]-1,2,4-triazolin-3-one;

4-methyl-5-[4-((2-(2-phenyl-4-oxazolyl)ethoxy)phenyl)oxymethyl]-1,2,4-triazolin-3-thione;

4-ethyl-5-[4-((2-(2-phenyl-4-oxazolyl)ethoxy)phenyl)oxymethyl]-1,2,4-triazolin-3-one;

4-ethyl-5-[4-((2-(2-phenyl-4-oxazolyl)ethoxy)phenyl)oxymethyl]-1,2,4-triazolin-3-thione;

4-iso-propyl-5-[4-((2-(2-phenyl-4-oxazolyl)ethoxy)phenyl)methyl]-1,2,4-triazolin-3-one;

4-n-propyl-5-[4-((2-(2-phenyl-4-oxazolyl)ethoxy)phenyl)methyl]-1,2,4-triazolin-3-one;

4-n-butyl-5-[4-((2-(2-phenyl-4-oxazolyl)ethoxy)phenyl)methyl]-1,2,4-triazolin-3-one;

4-methyl-5-[2-(4-((2-(2-phenyl-4-oxazolyl)ethoxy)phenyl)ethyl]-1,2,4-triazolin-3-one;

4-methyl-5-[2-(4-((2-(2-phenyl-4-oxazolyl)ethoxy)phenyl)ethyl]-1,2,4-triazolin-3-thione;

2-methyl-4-ethyl-5-[4-((2-(2-phenyl-4-oxazolyl)ethoxy)phenyl)methyl]-1,2,4-triazolin-3-one;

3-methylthio-4-methyl-5-[4-((2-(2-phenyl-4-oxazolyl)ethoxy)phenyl)methyl]-1,2,4-triazolidin;

1-[4-((2-(2-phenyl-4-oxazolyl)ethoxy)phenyl)methyl]-1,2,4-triazolidine-3,5-dione;

1-[4-((2-(2-phenyl-4-oxazolyl)ethoxy)phenyl)methyl]-1,3-diazolidine-2,4,5-trione;

and pharmaceutically acceptable salts thereof.

5. The compound 4-ethyl-5-[4-((2-(2-phenyl-4-oxazolyl)ethoxy)phenyl)methyl]-1,2,4-triazolin-3-one.

6. A composition comprising a compound of claim 1 and a pharmaceutically acceptable carrier, diluent or excipient.

7. A composition comprising a compound of claim 2 and a pharmaceutically acceptable carrier, diluent or excipient.

8. A composition comprising a compound of claim 3 and a pharmaceutically acceptable carrier, diluent or excipient.

9. A composition comprising a compound of claim 4 and a pharmaceutically acceptable carrier, diluent or excipient.

10. A composition comprising the compound of claim 5 and a pharmaceutically acceptable carrier, diluent or excipient.

11. A method of reducing hyperglycemia comprising administering to a patient in need thereof an effective dose of a compound of claim 1.

12. A method of reducing hyperglycemia comprising administering to a patient in need thereof an effective dose of a compound of claim 2.

13. A method of reducing hyperglycemia comprising administering to a patient in need thereof an effective dose of a compound of claim 3.

14. A method of reducing hyperglycemia comprising administering to a patient in need thereof an effective dose of a compound of claim 4.

15. A method of reducing hyperglycemia comprising administering to a patient in need thereof an effective dose of the compound of claim 5.

* * * * *